(12) United States Patent
Leigh

(10) Patent No.: US 8,475,809 B2
(45) Date of Patent: Jul. 2, 2013

(54) **COMPOSITION COMPRISING SORTASE ANCHORED SURFACE PROTEINS OF *STREPTOCOCCUS UBERIS***

(75) Inventor: James Leigh, Nottingham (GB)

(73) Assignee: The University of Nottingham, Nottingham (GB)

( * ) Notice: Subject to any disclaimer, the term of this patent is extended or adjusted under 35 U.S.C. 154(b) by 0 days.

(21) Appl. No.: 13/122,815

(22) PCT Filed: Oct. 6, 2009

(86) PCT No.: PCT/GB2009/051321
§ 371 (c)(1),
(2), (4) Date: Aug. 2, 2011

(87) PCT Pub. No.: WO2010/041056
PCT Pub. Date: Apr. 15, 2010

(65) Prior Publication Data
US 2012/0100174 A1  Apr. 26, 2012

(30) Foreign Application Priority Data

Oct. 6, 2008 (GB) .................................. 0818231.3

(51) Int. Cl.
*A61K 39/02* (2006.01)
*A61K 39/09* (2006.01)
*A61K 39/38* (2006.01)
*A61K 39/40* (2006.01)

(52) U.S. Cl.
USPC .................. 424/244.1; 424/165.1; 424/184.1; 424/185.1; 424/234.1; 424/237.1; 514/2.6

(58) Field of Classification Search
None
See application file for complete search history.

(56) References Cited

U.S. PATENT DOCUMENTS

2006/0073530 A1 * 4/2006 Schneewind et al. ........ 435/7.32

FOREIGN PATENT DOCUMENTS

WO  WO 98/21231  *  5/1998
WO  WO 2009/020391 A1  2/2009

OTHER PUBLICATIONS

Leigh et al (Vet. Immunology and Immunopathology. 2004. vol. 100:145-149).*
Egan, S.A. et al., "Identification of Sortase A (SrtA) Substrates in *Streptococcus uberis*: Evidence for an Additional Hexapeptide (LPXXXD) Sorting Motif," Journal of Proteome Research, Jan. 14, 2010, 8 pages.
Fontaine, M.C. et al., "Immunisation of Dairy Cattle with Recombinant *Streptococcus uberis* GapC or a Chimeric CAMP Antigen Confers Protection Against Heterologous Bacterial Challenge," Vaccine, 2002, pp. 2278-2286, vol. 20.
Leigh, J.A., "Vaccines Against Bovine Mastitis Due to *Streptococcus uberis* Current Status and Future Prospects," Advances in Experimental Medicine and Biology, Springer, Jan. 2000, pp. 307-311, vol. 480.
PCT International Search Report, PCT Application No. PCT/GB2009/051321, Mar. 10, 2010, 2 pages.
PCT International Written Opinion, PCT Application No. PCT/GB2009/051321, Mar. 10, 2010, 8 pages.
Talbot, B.G. et al., "Progress in the Development of Mastitis Vaccines," Livestock Production Science, 2005, pp. 101-113, vol. 98.

* cited by examiner

*Primary Examiner* — Ja'na Hines
(74) *Attorney, Agent, or Firm* — Fenwick & West

(57) ABSTRACT

The present invention provides an immunogenic composition comprising one or more *Streptococcus uberis* sortase-anchored surface proteins, or an immunogenic part thereof, wherein the composition is capable of eliciting an immune response, when administered to a subject.

16 Claims, 18 Drawing Sheets

| SCORE | APPEARANCE OF QUARTER | SCORE | APPEARANCE OF MILK |
|---|---|---|---|
| 1 | NORMAL | 1 | NORMAL |
| 2 | ABNORMAL (eg. Hardness) | 2 | SLIGHT ALTERATION (eg. A few flakes) |
| 3 | ABNORMAL (eg. Heat, tenderness,) | 3 | ABNORMAL (eg. Clots &/or clumps) |
| 4 | SWOLLEN (eg. Distended & discomfort on palpation) | 4 | ABNORMAL (eg. Changes in colour &/or composition) |

Figure 2

| Gene | Putative Anchoring motif | Additional comments |
|---|---|---|
| SUB0145 | LPXTG | Lactoferrin binding protein |
| SUB0164 | LPXTG | Pseudogene |
| SUB0207 | LPXAG | |
| SUB0241 | LPKAG | 2',3'-cyclic nucleotide 2'-phosphodiesterase |
| SUB0337 | LPATG | ABC transporter amino acid-binding protein |
| SUB0348 | LPHTG | Pseudogene |
| SUB0888 | LPPTG | |
| SUB1095 | LPSTG | Collagen-like protein |
| SUB1730 | LSPTG | |
| SUB1739 | LPTTG | Pseudogene |

Figure 3

| Gene[a] | Protein annotation | Putative sortase anchor | Molecular mass (Da)[b] | Exponential growth phase | | | Stationary growth phase | | |
|---|---|---|---|---|---|---|---|---|---|
| | | | | MASCOT score | No. of peptides matched[c] | Coverage (%)[d] | MASCOT score | No. of peptides matched[c] | Coverage (%)[d] |
| sub0135 | Putative fructan beta-fructosidase precursor | LPMTSDS | 142,956 | 41 | (1) | 1.4 | 541 | 10 | 11.3 |
| sub0145 | Putative lactoferrin binding protein | LPSTGDK | 57,829 | 1138 | 15[e] | 29.2 | 695 | 18 | 31.8 |
| sub0207 | Putative surface anchored protein | LPMAGER | 53,765 | 39 | 2 | 5.4 | 117 | 2 | 5.4 |
| sub0826 | Putative surface anchored subtilase family protein | LPETRDS | 168,468 | ND | ND | ND | 50 | 2 | 1.2 |
| sub0888 | Putative surface anchored protein | LPPTGSQ | 29,230 | 105 | (1) | 12.9 | 164 | 2 | 18.0 |
| sub1095 | Putative collagen like surface anchored protein | LPSTGDK | 47,642 | 59 | (1) | 1.7 | 88 | 2 | 4.3 |
| sub1154 | Putative C5a peptidase precursor | LPKTVDS | 127,957 | 68 | (1) | 1.7 | 111 | 6 | 4.8 |
| sub1370 | Putative zinc-carboxypeptidase | LPALADG | 116,563 | 507 | 7 | 10.6 | 2614 | 17 | 25.5 |
| sub1730 | Putative surface anchored protein | LPSTGED | 40,439 | 165 | 2 | 6.8 | 238 | 4 | 13.6 |

Figure 4A

| Gene[a] | Protein annotation | Putative sortase anchor | Molecular mass (Da)[b] | Exponential growth phase | | | Stationary growth phase | | |
|---|---|---|---|---|---|---|---|---|---|
| | | | | MASCOT score | No. of peptides matched[c] | Coverage (%)[d] | MASCOT score | No. of peptides matched[c] | Coverage (%)[d] |
| sub0135 | Putative fructan beta-fructosidase precursor | LPMTSDS | 142,956 | 286 | 5 | 5.8 | 1032 | 18 | 23.2 |
| sub0145 | Putative lactoferrin binding protein | LPSTGDK | 57,829 | 3047 | 17[e] | 27.0 | 746 | 15 | 28.8 |
| sub0207 | Putative surface anchored protein | LPMAGER | 53,765 | 50 | (1) | 2.4 | 163 | 4 | 11.2 |
| sub0888 | Putative surface anchored protein | LPPTGSQ | 29,230 | 209 | 2 | 18.0 | 118 | 2 | 18.0 |
| sub1154 | Putative C5a peptidase precursor | LPKTVDS | 127,957 | 153 | 3 | 3.4 | 237 | 10 | 14.4 |
| sub1370 | Putative zinc-carboxypeptidase | LPALADG | 116,563 | 146 | 3 | 4.0 | 1079 | 12 | 22.3 |
| sub1730 | Putative surface anchored protein | LPSTGED | 40,439 | 81 | (1) | 4.1 | 167 | 4 | 13.8 |

Figure 4B

MTKNRSSHSTYADKVIKGLSASCFILGAFVFAQQVSAEEVVTATNTSLTA
PTVTTVSPLTNTDVSATAVAADSIASPVTTTDSNLNSAPIIDTSNPSNITSPTD
TNTSTTSSDTTSSPIPVTLNKAAIASPTSQTETLASQEIYMDKVNQVTINTTV
NPATPMTWTIENYPNQTYNMQTGDFTGSPSYTVTSTSPNNSSVQIEIPPLFG
TDLSLRWPNNIRRTYRDYMGSYTLKGISEDGLTIVTKELILRPYADYMTHEE
LLNELNAIEANHATDRLVTIETIGQSALGNAIKMGIVAKDQASLDTYLNQTT
PMMLMDPDQALNLLAQGKFDYKLPILINNTHADEQPGIDVVRGLFKTFATE
SVINYQTVDAANNPTTVQIDIKALLDKVILLFNFTENPDGDIANTRALNNGL
DPNRDTGYQTNPETRAIVEQINKWNPISIFDVHGFVKEFLIEPCTPPHDPNFE
YDLFDASLVEGAREMGNAGITNSVYDSYIIPKFDYGSGWDDSFSGYTAVYG
LYQGILGHTIEIPETNQESYNAGYFAVLAGINYDLANSDQLMKNKLTFFSRG
IHKAEVAAAEEALLTVDGSVKGRIKDGHDTFFPDYYMIPMTLSTESDTDQA
FKMIDYFRRNGVILNELTADVAGYHKGDLVIDMAQAKRGFANHVLYKGAN
ESEWPAMYAELVMNFPAMRGFKADAIYADSLFAGNLGAVTLTSAPRTAPS
DKEYYIVSNNSLAAVQAVNAAIRAGKNVYLTNDGYVMDKATYESVIGTYP
LFAQATCMKPVGDTLKAIKVYAPGNPNLYLGFNSPSEVSLALNQMGFDVV
PSVDQADVIVLDNDQFDASILGKKPVIILGGSAMAKLESLGILTGFDAAMTS
ESDGSSYEGLMKISLDANSPYTSGYAANSLYYSNSGSWIEGVPTGFMTLANI
SASDFYVSGWWPNHEGLANKTVAISGLYQGQPMFIFAGNPVNKTHTINFYR
WVSNAIFGTNLTSFIEGQCTIPTDSETQVVRVNHNGQTVAVYQQVANKEVN
GTVSQNS<u>LPALADGS</u>HKDDSKLFWVTGLLVASGGLFAALKRRED

Figure 6A

MRKFYYKEKKMEIKQKHGKHALRKAVTAAVLAGTAFSSLGGFAGAVT
TVKAEDLFTINNSEVQDKLESKVKQLLEAQRKGEDISEKLRELLSELPTDILK
DIMLSNIEADYLLGFLKPAVEEMVRRSEQNDERWKDITEKTLALEALKDSE
REIRKEKEKLEDEVQLAKVKIETKESELNDLKKDYIDTREELADTIEELDEV
KNSIVEKEAKVKGLEEKLRDLEKELGDYDKKLSEAAKQNSDLSNENKELKE
NLDTAENITVELQKKSHELEKTKKEVELELKAEKEALEAEKVKLAEANEAN
DKLSEERDAAKKEAEKVPELEGQVEKLVEEITAAKKEAEELQAKAEGLEKD
FEAVKAEKEALEAEIAKLKEDHQKEVDALNALLADKEKMLKSLQEQLDKA
KEEAMKNEQMSQEEKAKLQAELDKAKQELAEKIKDMPNKVAPQAEGKAN
AGQAAPNQNQNNQAQANQAKNANN<u>LPSTGDKP</u>VNPLLVASGLSLMIGAG
AFVYAGKRKKG

Figure 6B

MKQEKKCVNWFMRKRGKQWIYGCGILICGLVFGVEATSVAAETIPTTA
TVETLNSDVTSKTSQETQKTTEIATPVSEIVMPSQQKVVEEVTQEVSVQNQE
TVINMPVLTQGVNIAGPNETAILTDSIVQNNVQPIDRVEKMETSFSTELTKK
AESSYNTNLQDLNYDPNVWEVREDGLYSNAVGKGDNFLFSASTGENFIFQT
DVTFLQNTGAASLVFRSNNDPENLNGYVVNLDGNSHKARLWRWAEANLI
NDKEILASPDNKYFLKVVATNGWISYYINGILIANLSDYTIQRDDLGQTTYIK
DGHFGLLNWNGEMVFQNTFYRELTNEELPLLNDVTVTSKNGPVEPKGQFF
SESSVYIQYVSNDASTVDLSFDANNSDALITVTDAHGKVYSNPSAIPVTVGP
NYLTVTSTYTTTDGYVIPSTYRINVHRRQPQSVYYNENFRDQYHYSVKDGW
ANDPNGLVYYNGVYHMFYQFYDDTKWGPMHWAHATSTDLIHWEDQPIAF
YPDYNGTMFSGCIVADVNNSSGLFDSENGGLVALITINGEGQRIKLAYSTDE
GKTWQKVDEIVADWTTDPLQTRDFRDPKVFRWENKWFMVIAGGPLRLYSS
DDLKNWTVESTYPDLHTECPDLYPVLAEDQTVKWVLSRGGRYYKVGDLQ
QADGNWKFIPDANYQETDSIMNFGKDSYAAMTYYVQDFGTKANPTIPKIIE
LNWMNTWDNYCNLVADRLGQSFNGTFNLNLELGLVKEGDKYVLTQTPVE
AYESLRDNDNKVEYKNVVVGKENDLFKDFSGDTYEIVAHFKPSDKTTKVG
FNLRVGSGEMTKVYYDLIAGRIIIDRSQSGIILTELFSNIDSQAVTPNIDGSIDL
HIFVDRASVEVFSKNHTVAGANQIFTSAQSLGLEVLIDGEDAKADIVLYPLK
SIWKNKIIDTTPQIVIPASEPKVRMNVGDSTTVKAYVSPVGASQDLIWNISNP
SLVLDQISGNQVFLKAIKKGQVIVRAQSQSNPAVYQDFIIDILEDNFNTNVKD
VNVFSGDWYVDGESLKVANHNSNDIYMSADKIPYENYQMDLDIKYGRGIV
NIFFASGNPDANNAYTIQFGSNNSVRLFRFYRDTIFEAPMIDVINDNQFHHV
RLVKSANVIHVYVDNEMVMSYTFDQVEEFFNNPYLGLGLWDGELAVQNF
YVIDLDAQKPVFVEEHEKEKLLSELKKSVVKTSSYSTLKTIETSSKTNSENLE
APTVSKKN<u>LPMTSDS</u>NNNLEELGILVILTTLGAFLGRVILKKEK

Figure 6C

MKKKQEMKYYLRKSAYGLAAVSVAVLAVGSPVSAQEKAASTEATPKVA
PKVPEKPSKEVIKKALKKTDEETKEKEKEAKEKVENSEESTAMVSELSSTNE
ETSSEEENNTDEEETDGLESEESEETESEVKEESEEEKEDDPSESDTEVENVE
AINLSEAEGNDSSKPETSEEVTAEEDRQETDRLAEVKTEESAKEGDEDADK
KDEAEEKAKKGAELSRVKAEALAKLEALNASRLMKKIVESGKTVEGILSFM
KESLPQLEAARASEQAKAPEVTQSPDHLPSEKKAVHNPVQVAKRSESLEQK
AENAKTSTNLQNTQIPVQEAKRTQAQ<u>LPSTGED</u>YQAYLVAAAMALIASSGM
VAYGSYRKKKQK

Figure 6D

MSKPMTKKKKAISIQKSVKPILGFTFGALLLSTVFTPSVFAEEVVSSLGHA
TSGLLSVSVPKELTSLETTTYLMASESPSNTLTSDTISSDNGGTASNPNEIVTT
ETTSEAIPFDTEVIQNPDLPIGEIKVVQEGVAGEVTVTKTTTTITLNGVSQSTT
TESRVPVKKPINKIIEVGTKEISTSPSSSDVITVSPSPSSTSSESNQQGSLTPAPK
SRQNSQEKKGSQTKKSKDDAKEKEGDKKE<u>LPPTGSQ</u>ESGIFSLFSALISTALG
LFLLKSNKND

Figure 6E

MKSYLKRRYGLITTSVLAATVLATGWQSTSVLAENPTTSPTTTVTSNGFN
FNATLLDHNGKTVSGKTVSLYDITDGNRTLVQSAVSDQNGIASFSQLPLNR
NLSVFVDNVAQGYTTRTSESGQVRSSAFYIDGQGTNTPKYSDKTITISVLNE
EAEPLANQKVTLTNPLKEVVGEAMTDADGHVVFKDKLLEGVFYNYAVNG
KAIDSAQPDSKRSVFLESNQLAKEGFTFTATILGKNGKTVAGKTVSLYDITD
GNRTLVQSAVSDQNGIASFSQLPLNRNLSVFIDDVAQGYTTRTSENGQVRSS
AFYVDGQGTNTPKYSDKTITISVLNEEGEPLANQKVTLINPLKEVIGEANTD
ANGKVIFTDKLLDGVFYTYAVNDQTIDATQPDTSRNVFLRADQILKESPKN
TASEAATNLEKTTESKEGNMPQQNQSEAKEKAPEKQVDANAANKKAPGHG
EAKKG<u>LPMAGER</u>GSRLFTFIGLSLILGIAGYLLKHKKVKS

Figure 6F

MVKNNIHSRKKHILKISLLATSVLTTTVSTVSAEQLQNEKQSDLLSKMTET
STPHTIISSEDLSNSNQEANQKDETASKSLQPMIEKVDPSHIQALWEKVGTGE
GDVLAVIDSGIETKHSMLQLPEDADKMYTDQASIDSKKQLLGIERGQWIND
KLPFYHDYTQGEESIDRNTYHGTHVAGIATASGLTQKENKEQMQGIVPNAQ
LLFLKVGQPSVEGEREKHYAMAIKDAIALGATAINMSFGQVGKASHELNDD
FKKALALAADKGVAIVVAAGNDYAMGGSQTKPLAKNPDTGVIGTPATTEE
VFTVAAYVAPHYWSRVLSVTDGSTSKALALEMASPFAENKDYELIFLEKGL
ETEENAERLKNKVLVLNYDFVTNSKEVAEKVEALGAAGVLVHNNQAKKPL
IPLAYNGPLPMGFISKEDADWLKTMTSPQFRLKKEKQLVEVPGGRQMTNFS
SWGLSVDGNMKPDFAAPGYEIYSPTPGNDYSKMSGTSAASPHAMGIIHLVR
KHIQKEYPHLSAKEQLQLVKNLLMSTASPIYSELDHSYYSPRVQGAGALDA
KKALETDVYVTAADGLSKIQLGDVNNQFELRVTLHNLSNQEKNFTYFARV
LTDKVEKGRILLRPQELYQTRPLQVKLAPNQKQEVVIKVDISNFDQQLKAQ
MPNGYFLDGFVVFQSKEGAQKDLSIPFIAFKGKFADLEALDSPIYRNLDGTF
YYSPKEGQDPYDFEVDSIQQIKEQYMTGLITTFTPWSLVEGSKIDGFSPEMA
SEFSTTDYLGSYNKEGDNTVRRFRFVEGKPYLALSPNGDDNMDKVGFRGV
FLRNVRDIKAQVFASDDLQHPIWESPIKAFAKKDVNTNDIKESMLENTVWE
GKDASGNPVTEGLYRYRVTYTPLAEGAKEQFIDFDILVDLTPSKLPQSAILM
LAERRIELTESRDYLSHDTYRDRLYYKGTDDINFTTFEKDDMGHFVIPNQ
VEDELSGEKITINLDKTDHFFFVREDFSGNFSVISLSQLLNNHSDQMHSLEES
KSDRKESNTGDIRHEKQENLSQQTLLSTPSIDGQKQNDQLMVEKEKDIMDE
SKSERSEKNKFPKVPASITLKDGTLYPQSISQKTS<u>LPKTVDS</u>QKTMTFLGIAM
LFGGILQVLWSYFKKRD

Figure 6G

MTHMNNNGRYKQRFSLRKYKFGAASVLLGTIFALGMTGTTAQAQMPSH
SHPGGVYPGGIIPGAPGAIPGIPGGGSGFDFDPSGYPAGPHGYLPSYGPGGVG
MLQGPPGPAGPIGPNGIPGERGPVGPAGAEGPRGPKGDKGETGQQGPRGEA
GIAGPSGPQGPAGVAGPAGPQGVAGRDGRDGRDGRPGEAGLDGLDGLNGL
NGIDGTDGKDGKDGKDGQNGQDGKNGRNGQDGQKGKDGQNGRNGQDGK
AGKDGKSGTDGKNGKAGTDGKNGKSGKDGKAGTDGKNGRAGTDGKNGK
AGQDGKDGKNGTDGLNGRDGRDGRDGRDGRDGLDGKDGKNGKDGESPII
NVKDNGNGSHTITFLNPDGSRKEVTISNGKDGQPGRDGKDGRDGKDGMPG
RDGMNGKDGQAAAGNTAGKGNASDMKPKAMAAPAAMTNQNAHANNNG
PAKAQ<u>LPSTGDK</u>ANPFFTAAALAVMASAGMVAVSRKRKED

Figure 6H

LRYKKMTRSSNSRIVLQSTLIMIFASSCVNHFKGTIHADEKVINGSEASIQV
DYTLNTASENRQIPEEKVTEEATNDQPELLEKQAAFLHEGREKNTENLPLD
GRGSLIASIDSGVDIKHEAFANNDDNHDFHKETEVSEGSTSKIPFVYDFLSGD
TSVRDDEEEHGMHIAGILVGDSKKGFKGMAPKAQLIAYRTWSKNNSEGYQ
EANQFFAMKDAIKRGADVISLSIGEIGSGQNDDIWAKVLEEAKKKNVVVA
AMGNYGTSATSNTFDQVVDETFPQTDSSTLLSVSANPEVIGVGSIFEKEMYL
PTLKIDTLEVPYENINWQNYYLFKQEKQERISFNEMLITLNQSKEEGSLKDK
VVIIERQAENIFPQLKEVMKKGAKGVILNQSGPTTYGNYETVPELRNTLLD
DEDGDFKKTWAVSISANDGKALKDYLQKQDKKKSYSLVFNTKPQLKHVFK
YPGVSGFSTWGPGLDLTLKPDIVAPGENIYSTGNDNSYFISSGTSMSAPKVA
GASAMFLPVTKKWQKKWEKQNVSMSIPQLTKLLFQNTADILYDHSVPNGK
PILPYSPRRQGAGALNVKKAAQTNVFVTSADNKGAILLKDFKESRKEFDIVI
RNFSDQVRRFKIEPGSVLGKILYSKDRKNYDKNETIQTVHSRVIKDSAIESPL
YVQIAPNSSMILPLKLNVGKAVENEFVEGFIKLRSLEKDQPDLNIPMGFYGD
WNSENILDPVAWQEGSKTRLTGIVHPYGLGEDKFDIVPWGVDYEKWKQDP
KALDADQRFYVMQSQAGIANHAKMRLRLIFMRHAKDYRVDILNSQKDKVL
KTLKTGHQAPKYMESALLEHGDQYQMQFADFDPDLEWDGSVYNPKTNTE
DPLPDGNYFIRVSSRISKNRPYQEHIIPFAIDNQKPKVKIEEKTALQVVFHVD
DAHLQGIRLVKDNKIIQTLETDTQGRFRLNLADFQGKGFELEAIDFAENKTII
DLDSLKEKEVGYLFGASSSYNKSRYRSPRSVAHKNAEDILHENSEESEEIASA
LTFEDGSDFHDGKKTNAYSEINKSNDNSVHLKDNTYYRDYYIHLKEGQRLL
VTTTNAFHNSKQGNDITAPTWQANYTYDPSTNQGQYYRKIAIPIYQGSNTIN
VKAFYKDKLIFNKGYAVKLDTEVPQLTFDNPNISFTSDKWQNLSDDEYDDD
NIVGTITIPNNTLRLSGKIRDGLDGWRMFINGDMVDSDIKLGEYDDIFQQNR
RQWKYEKQVENDDYVLIKLSDHVKNSRSYLFKVKIDPTVSEYHFTNKNDII
DDDKTLLTLNTLTDSSLGYANKLLNMPKDLVKSTDDLFKAMTMLFKKESF
FLYPLKNDLNTNGISMMTSLVQFQAKDVKENIPLEWEIKTKASDSRQLLYQ
NLKNEKERLDQVSTNPLAHQLPLENSNQENGQDAILTSTKVLPMSKSSIFRD
SLRETS<u>LPETRDS</u>SSMANWSLAFFLSAVICFFKGRRKRLNKL

Figure 6I

MENQNQLTLQGILGKCLKWFLLLSISLFTAFPFIWMLISSLKTKAEVMNTEV
IWPHIPQWGNYLEIFTQSPIPKYIWNSLWTSVVIVLIQIVTGAMLAYALVFLR
FKGRQLIFAIVMGTYMLPAAATYIPSYIILSKGGMLNTLTGLIVSSTISIFGIFL
LRQAFMQVPRSLIEASRMDGASHFRVLWEIVCPMTKSSFITFGLMSFIAAYN
SGKETSIGDVTLTFSKELVPVPNIDEEIVIPSIPEKPLVEPEVDSILPLIPLQPSL
PIYPSPDLPEMEQPDQDSPEISGQSQIVDIVEDTLPGVSGQQSSSEETEITEDT
RPESDNEIIIGGQSELVDIVEDTQSGMSGQHSSSEETEISEDTRPESDNEIIVGG
QNELVDIVEDTQPSLSGHQSESQETVTVEDTQPNQTNILIGGQSEIVDIIEDTQ
AGMTGQYSSTDQLTIVEDTLPEQMEETDEIKSDSQVMDIPKVNDTNNDKGA
KASVAFDVEESKVVTTQDIKPSTYVKGDNQLPQTGDDDNVNAFFTLAALSV
IGATGLRQNKRREKERN

Figure 6J

VVKVTVDGSDNSTIDSGFVKVEQPTPGSNSSSESLSQSTTQSSSQSSSAKPVA
SQTAAELPHTGQAENNGLYGSAALAILAALGLAGKKRDEK

Figure 6K

MFKTKKEIFSIRKTALGVGSVLLGVILTTQVASANEVSLMTPSVDKSLTTTSP
VLESTSSQLAATTAPTTTDTTSNVTATSPVLAAATTAPSVTTSPIASPIRYVS
DPNQPVGYRATQVQGTDGSIITTQTGALDANGNPIVTVERIEPTKTVIVLGT
KSTSQVTSTQAATTTYSIDVTKPVGTDVVIPAVDGQTTTTTYKIETATTAP
VSPSVLSEGYKWIDQPFYHVDTTQTLPSDRISIDQLFVPMPVLTPDYNTTEST
VREYAQYAENYMYDYITVTNPDGSTTRQQVIRPVTSEMLDPTNTRLRTLTG
LTDDNAFYSRLFDASQQDLWNTSAQDYGLEIVPEDLSTSTDDFLRYHSSNII
NDALYVDIKADYLRAQLAYDLVSLGTLTSDQQSAMDMMTSQFESLTLRYN
NYKDSVAIVVDYSNTTMSATQADFEAKLAALPVEVQRAISELTIYDGQIPG
MGETTLGLANSADQTIALKYEANNLNLVSTVLHEMTHIIDFKSGLYSETTD
RNTDGSLSTVMAFSDTQEFLDVYHTYFDRPDVWSYYRDNSEEAFAEGLSQ
YIMHRLFGTPYSTYIANPYTGDAYNPGDGSGYSPFAETEFYFASLYNRLFEY
PRTAQVVPYLVTTTTTAPVNGQVIYGAMPEETTTTTPYTTVYVGDTSFAYD
PTGQTDRVQAGVDGTETIRTTYSLDSNNQLVATQTVISSTPVQNQIITKGTQ
PTVVDTSVPMTIVYQEVTDGSLGDWQVNVLDAGQDGLIRSTTTYSVDPVTG
IVTPSTTEATITAMRPMIVQYQVGSEKVTAIPYQTRYVIDTSLATGTQVIVQE
GVNGSSTESVQSYNFIQDGSNSRFDAIVYASPVVVAAQDQVIAVGGQDQVT
DQAVAKTIFYQEVTDGSLGDWQVKVLDAGQDGLVRTTTSYSVDPVTGIVT
PSTTEATITAMKPMIVQYQVGKSKLSAIPFLTEYITDDSLAVGLEKVIQEGVG
GTQIETVQSFNFIQDGANSHFENIVYSSPTIVAAVDQVIARGTKVVEVVVA
VPEVVTPKPETSEVISPEKGQTAPTITVEAIKAPAQKKAKVEVVTTPKESLPT
TGDDQNLLVTLMSSLLLMSLGLGLKKKEDE

Figure 6L

LLALSQLPDKLLEKIDITCFDDPKHFGRGIPFQEDSSTAWINSPIDAISYDYHD
MNDFQNWMEQKGLDTDQSYVPRSLYGRYMTERAHDLLQKLKASVIHEKV
TQLNYEPDSQKWNIGTSQRTIPTRFDEVHLTCGELPVLDPYHLQGNPNYIAD
PYPLKNLPKQPGKKDRIAIIGTGLASIDTLKWLLKNSQADLLAFSPSMTFPTV
RILKKETIDWQFLTDTNKQKLFEENSFNFKSLENLFLSELQALGFQNWEETC
RQFLAEGIPGISLSLAFPAQLFLLQQLASHLVDWLTDFWPQMTLSDRQYYK
ENYGKAIINLRNPMPEEAGRLLIEATAQGRLQIIEAVTDIEAGNYGFVLKRE
VGKELSVATVINATGYHLKESNVHQARTLIQQVIRDGLVQINPEGGLSILPQ
TGQVISPKYGILATLYAHGSLVNGVIYQNNSTIKIQQMAERAIGNVIKKPTI

Figure 6M

MRKHYVSKSAIFLAMLVATGSAQFVKAETPTTTTSPATSLTDASASTTPTTN
TTSTVTPALDPNTNFTVDSSATTSTTTPSPVEAAAISPVIATAQPTTNVTSAS
LAPAANTMATTPVEGQTVDVRIISTTDLHSNLVNYDYYQDKASQTIGLAKA
AVLIDQAKAENPNAVLVDNGDILQGTPLGTYEALIDPLQPGEVHPMYAALD
KLGFDASTLGNHEFNYGLTFIENAIASAGLPILNANVFDAATGEYLFQPYAI
VTKSFTDANGQAVDLKIGITGIVPPQIMLWDKANLEGKVTVKDAVQAVTEII
PTIKNAGADIVLVLAHTGIGDDVYETGEENVGYQIASLAGVDAVVTGHSHA
EFPSGQDTGFYESYNGVDGVSGLINGTPVTMAGKYGDHIGIIDLNVSYTGG
KWTVNRDKNHAEIRKIDTKSTIADADILALAQASHLGTIDYVRQTVGETTAP
INSYFALVKDDPSVQIVNNAQLWYAKQQLAGTPEADLPLLSAAAPFKAGTR
NDPTAYTDIPAGPIAIKNVADLYLYDNVTAILKLTGADIKEWLEMSAGQFN
TIDPNVAGPQNLVNTDYRTYNFDVIDGVTYEFDVTQPNKYDAKGNLLNPN
ASRVRNLKFQGKEIDPNQEFMVVTNNYRASGSFPGVKNATINRLLNLENRQ
AIINYIVSEKTINPSADNNWYFADTIQGLDLHFLSADTSKNLIGDKADISYTG
PSTIEGFGDFVFTYVKPELPVATPETPQETGSQLTENRRQEIHQLATRVYNQ
TKATSSSTTKAELPKAGSQESKGLFFMGLSLLGLAGLITKKEERQ

Figure 6N

MRKFLMSCFAALLLLFAGVSQADADQYLRVGMEAAYAPFNWTQDDNSNG
AVPIEGTNQYANGYDVQVAKKVAKSLNKKLLVVKTSWTGLIPALTSGKIDM
IAAGMSPTEERKKEIAFSDSYYTSEPVIVVKADSKFAKAKSLDDFAGAKITA
QQGVWHVNLIPQINGVKAQTPMGDFSQMRQALSSGVIDGYISERPEAMTAE
NANSAFKMVVLKKAFTVNESDAAIAVGMRKDDPRIVQVNTVLADLSANDR
LDLMDKMVTLQPKEKKAENGVQPSFLDQMWSIVTKNWKQFLRGTGLTLLI
STIGTIVGLIIGLLIGIYRTAPKSKHKVLAFFQKLFGWFLNVYIEVFRGTPMIV
QSMVIYYGTAQAFGISIDRTLAAIFIVSINTGAYMTEIVRGGIFAVDKGQFEA
ATALGFTHGQTMRKIVLPQVVRNILPATGNEFVINIKDTSVLNVISVVELYFS
GNTVATQNYQYFQTFSVIAVIYFILTFTVTRILRYVERRIDDDNYTTTVNELP

Figure 6O

COMPOSITION COMPRISING SORTASE ANCHORED SURFACE PROTEINS OF *STREPTOCOCCUS UBERIS*

CROSS-REFERENCE TO RELATED APPLICATION

This application is the National Stage of International Application No. PCT/GB2009/051321, filed Oct. 6, 2009, which claims priority to Great Britain Application No. 0818231.3, filed Oct. 6, 2008, which are incorporated herein in their entirety.

The present invention relates to an immunogenic composition for use in eliciting an immune response to *Streptococcus uberis*, and in particular, to immunogenic compositions capable of eliciting a protective immune response.

*Streptococcus uberis* (*S. uberis*) is currently responsible for around 20-30% of all clinical mastitis cases in the UK and occurs at a similar incidence worldwide. Mastitis remains the most economically important infectious disease of dairy cattle throughout the world. The annual loss due to clinical mastitis in the UK has been estimated at approximately £170 million and between $1.5-2.0 billion in the USA. These losses can be attributed to a reduction in milk production, the associated costs of treatment and the culling of persistent and repeatedly infected cows. Micro organisms that cause mastitis can be divided into those that show a contagious route of transmission, such as *Staphylococcus aureus* and *Streptococcus agalactiae*, and those that additionally infect the udder frequently from an environmental reservoir, such as *Escherichia coli* and *Streptococcus uberis*. The application of various control measures over the past two decades, based on improved milking practices, post-milking teat disinfection and routine intra-mammary anti-microbial treatment after each lactation, has proved effective against pathogens with a solely contagious route of transmission, but has had little, if any, impact on the incidence of infection of the mammary gland from environmental reservoirs. The failure to control bovine mastitis caused by *S. uberis* is largely attributed to insufficient information on the pathogenesis of infection.

Bovine mastitis, which causes inflammation of the mammary gland (udder), usually arises as a result of intramammary infection by bacteria. The signs of mastitis vary according to factors in the host and the invading pathogen and intramammary infection may result in sub-clinical or clinical disease. Sub-clinical mastitis, by definition, shows no obvious signs of disease. Infection associated with clinical disease can range from visible abnormalities in the milk (protein aggregates or clots) accompanied by pain and swelling in the affected gland, to production of a secretion which is composed solely of aggregated protein in a serous fluid. In severe cases, there may be systemic signs such as elevated temperature and loss of appetite, which may develop to bacteraemia, septicaemia and lead to death of the animal.

Milk from an uninfected mammary gland contains leukocytes, including macrophages, neutrophils and lymphocytes typically below 150,000 cells/ml. Infection usually results in a localised inflammatory response, characterised by the influx of neutrophils into the infected quarter of the mammary gland and milk. The resulting milk cell count is used internationally as a surrogate measure of infection of the mammary gland and as a measure of milk quality and udder health. Milk from sub-clinically infected quarters usually has a cell count in excess of 250,000 cells/ml but this figure may vary widely. Milk from clinically infected quarters usually contains in excess of 2,000,000 cells/ml. The interaction between bacteria and/or their products and the large number of neutrophils in the secretion has been considered to be the principal cause underlying the decreased rate of milk production, degradation of the secretion and the induction of widespread inflammatory changes characteristic of mastitis.

One aim of this invention is to provide one or more compositions which can be used to elicit a protective immune response to *Streptococcus uberis*, and thereby prevent or reduce the incidence of mastitis.

According to a first aspect, the present invention provides an immunogenic composition comprising one or more *Streptococcus uberis* proteins, or an immunogenic part thereof, wherein the composition is capable of eliciting an immune response, when administered to a subject.

Preferably the one or more *Streptococcus uberis* proteins are sortase-anchored proteins, or an immunogenic part thereof.

A *Streptococcus uberis* sortase-anchored protein refers to any protein which in wild type *Streptococcus uberis* is anchored to the surface of the bacteria by the action of the enzyme sortase.

The one or more sortase-anchored proteins, or the one or more *Streptococcus uberis* proteins, may be selected from the group comprising the proteins SUB0145, SUB1095 and SUB1154 or a protein with 50%, 60%, 70%, 80%, 90%, 95% or more, preferably 80% or more, sequence homology with one of the aforementioned proteins.

The immunogenic composition may comprise two or more *Streptococcus uberis* proteins, or an immunogenic part thereof.

The two or more sortase-anchored proteins, or the two or more *Streptococcus uberis* proteins, may be selected from the group comprising the proteins SUB0145, SUB1095 and SUB1154 or a protein with 50%, 60%, 70%, 80%, 90%, 95% or more, preferably 80% or more, sequence homology with one of the aforementioned proteins.

The immunogenic composition may comprise proteins SUB0145, SUB1095 and SUB1154 or a protein with 50%, 60%, 70%, 80%, 90%, 95% or more, preferably 80% or more, sequence homology with one of the aforementioned proteins.

The immunogenic composition may comprise proteins SUB1095 and SUB1154 or a protein with 50%, 60%, 70%, 80%, 90%, 95% or more, preferably 80% or more, sequence homology with one of the aforementioned proteins.

The one or more sortase-anchored proteins, or the one or more *Streptococcus uberis* proteins, may be selected from the group comprising the proteins SUB0135, SUB0145, SUB0207, SUB0826, SUB0888, SUB1095, SUB1154, SUB1370, SUB1730 and SUB0241 or a protein with 50%, 60%, 70%, 80%, 90%, 95% or more, preferably 80% or more, sequence homology with one of the aforementioned proteins.

The one or more sortase-anchored proteins, or the one or more *Streptococcus uberis* proteins, may be selected from the group comprising the proteins SUB0135, SUB0207, SUB0826, SUB0888, SUB1095, SUB1154, SUB1370, SUB1730 and SUB0241 or a protein with 50%, 60%, 70%, 80%, 90%, 95% or more, preferably 80% or more, sequence homology with one of the aforementioned proteins.

Reference to percentage homology relates to the percent identity between two aligned sequences. The percent identity refers to the residues in two proteins which are the same, when the protein sequences are aligned for maximum correspondence and when inversions and translocations are accounted for. Preferably the percent identity ignores any conservative differences between the aligned sequences which do not affect function. The percent identity between aligned sequences can be established by using well-established tools (such as the BLAST algorithm—Basic Local Alignment Search Tool; Altschul et al., (1990) J Mol. Biol. 215:403-10)

In one embodiment one or more of the sortase-anchored proteins, or one or more of the *Streptococcus uberis* proteins, is SUB0135. In another embodiment one or more of the sortase-anchored proteins, or one or more of the *Streptococcus uberis* proteins, is not SUB0135.

In one embodiment one or more of the sortase-anchored proteins, or one or more of the *Streptococcus uberis* proteins, is SUB0145. In another embodiment one or more of the sortase-anchored proteins, or one or more of the *Streptococcus uberis* proteins, is not SUB0145.

In one embodiment one or more of the sortase-anchored proteins, or one or more of the *Streptococcus uberis* proteins, is SUB0207. In another embodiment one or more of the sortase-anchored proteins, or one or more of the *Streptococcus uberis* proteins, is not SUB0207.

In one embodiment one or more of the sortase-anchored proteins, or one or more of the *Streptococcus uberis* proteins, is SUB0826. In another embodiment one or more of the sortase-anchored proteins, or one or more of the *Streptococcus uberis* proteins, is not SUB0826.

In one embodiment one or more of the sortase-anchored proteins, or one or more of the *Streptococcus uberis* proteins, is SUB0888. In another embodiment one or more of the sortase-anchored proteins, or one or more of the *Streptococcus uberis* proteins, is not SUB0888.

In one embodiment one or more of the sortase-anchored proteins, or one or more of the *Streptococcus uberis* proteins, is SUB1095. In another embodiment one or more of the sortase-anchored proteins, or one or more of the *Streptococcus uberis* proteins, is not SUB1095.

In one embodiment one or more of the sortase-anchored proteins, or one or more of the *Streptococcus uberis* proteins, is SUB1154. In another embodiment one or more of the sortase-anchored proteins, or one or more of the *Streptococcus uberis* proteins, is not SUB1154.

In one embodiment one or more of the sortase-anchored proteins, or one or more of the *Streptococcus uberis* proteins, is SUB1370. In another embodiment one or more of the sortase-anchored proteins, or one or more of the *Streptococcus uberis* proteins, is not SUB1370.

In one embodiment one or more of the sortase-anchored proteins, or one or more of the *Streptococcus uberis* proteins, is SUB1730. In another embodiment one or more of the sortase-anchored proteins, or one or more of the *Streptococcus uberis* proteins, is not SUB1730.

In one embodiment one or more of the sortase-anchored proteins, or one or more of the *Streptococcus uberis* proteins, is SUB0241. In another embodiment one or more of the sortase-anchored proteins, or one or more of the *Streptococcus uberis* proteins, is not SUB0241.

In another embodiment one or more of the sortase-anchored proteins, or one or more of the *Streptococcus uberis* proteins, is not SUB0164. In another embodiment one or more of the sortase-anchored proteins, or one or more of the *Streptococcus uberis* proteins, is not SUB0348. In another embodiment one or more of the sortase-anchored proteins, or one or more of the *Streptococcus uberis* proteins, is not SUB1739. In another embodiment one or more of the sortase-anchored proteins, or one or more of the *Streptococcus uberis* proteins, is not SUB0206. In another embodiment one or more of the sortase-anchored proteins, or one or more of the *Streptococcus uberis* proteins, is not SUB0337.

An immunogenic part of a protein refers to a part of a larger protein which is capable of eliciting an immune response. Preferably the immune response elicited will recognise the part of the protein and the whole protein. Preferably the immunogenic part includes at least one epitope from the full length protein.

An immunogenic composition is a composition that is capable of eliciting an immune response to an antigen in the composition when the composition is administered to a subject. Preferably the immune response elicited is protective. Preferably the subject is a mammal, more preferably a ruminant, such as a cow, sheep or goat. The antigen in the immunogenic composition of the invention may be one or more proteins which are anchored to the surface of *Streptococcus uberis* by the enzyme sortase.

Preferably the immune response elicited by a composition of the invention is directed to the antigen in the composition and acts to prevent or reduce infection by *Streptococcus uberis* in a subject to whom the immunogenic composition has been administered. The immune response may recognise and destroy *Streptococcus uberis*. Alternatively, or additionally, the immune response elicited may impede or prevent replication of *Streptococcus uberis*. Alternatively, or additionally, the immune response elicited may impede or prevent *Streptococcus uberis* causing disease, such as mastitis, in the subject. Preferably, the immune response elicited by the composition is also capable of being directed to strains of *Streptococcus uberis* other than that from which the proteins in the composition are derived.

The immune response generated may be a cellular and/or antibody-mediated immune response. Usually, an immune response includes, but is not limited to, one or more of the following effects, the production of antibodies, B cells, helper T cells, suppressor T cells and/or cytotoxic T cells, directed to the one or more immunogenic proteins in the composition.

The composition may also comprise a further one or more antigens, in addition to one or more *S. uberis* sortase-anchored proteins, or one or more *S. uberis* proteins. The further antigens may also be capable of eliciting an immune response directed to the pathogenic organism from which they are derived. The further antigens may be derived from *S. uberis* or they may be derived from a different pathogenic organism.

The composition may be used to elicit/produce a protective immune response when administered to a subject. The protective immune response may cause *S. uberis* to be killed upon infecting a subject, or it may prevent or inhibit *S. uberis* from replicating and/or from causing disease in a subject.

The composition may be used as a prophylactic or a therapeutic vaccine against *S. uberis*

According to a further aspect, the invention provides a pharmaceutical composition comprising one or more *S. uberis* sortase-anchored proteins, or one or more *S. uberis* proteins, or part thereof, in combination with a pharmaceutically acceptable carrier or excipient.

Preferably the pharmaceutical composition comprises a composition according to any aspect of the invention.

Preferably the pharmaceutical composition is capable of producing a protective immune response to *S. uberis*.

The phrase "producing a protective immune response" as used herein means that the composition is capable of generating a protective response in a host organism, such as a cow, to whom it is administered. Preferably a protective immune response protects against subsequent infection by *S. uberis*. The protective immune response may eliminate or reduce the level of infection by reducing replication of *S. uberis* by affecting the mode of action of *S. uberis*. Preferably the protective immune response reduces or prevents disease caused by *S. uberis*.

Suitable acceptable excipients and carriers for use in a pharmaceutical composition will be well known to those skilled in the art. These may include solid or liquid carriers. Suitable liquid carriers include water and saline. The proteins of the composition may be formulated into an emulsion or they may be formulated into biodegradable microspheres or liposomes.

The composition may further comprise an adjuvant. Suitable adjuvants will be well known to those skilled in the art, and may include Freund's Incomplete Adjuvant (for use in animals), and metal salts, such as aluminium or calcium salts.

The composition may also comprise polymers or other agents to control the consistency of the composition, and/or to control the release of the proteins from the composition.

The composition may also comprise other agents such as diluents, which may include water; saline; glycerol or other suitable alcohols etc; wetting or emulsifying agents; buffering agents; thickening agents for example cellulose or cellulose derivatives; preservatives; detergents, antimicrobial agents; and the like.

Preferably the active ingredients in the composition are greater than 50% pure, usually greater than 80% pure, often greater than 90% pure and more preferably greater than 95%, 98% or 99% pure. With active ingredients approaching 100% pure, for example about 99.5% pure or about 99.9% pure, being used most often.

The composition of the present invention may be used as vaccine against infections caused by *S. uberis*. The vaccine may be administered prophylactically to animals at risk of exposure to *S. uberis*, and/or therapeutically to animals who have already been exposed to *S. uberis*.

Preferably, if the composition is used as a vaccine, the composition comprises an immunologically effective amount of antigen (comprised of *S. uberis* proteins). An "immunologically effective amount" of an antigen is an amount that when administered to an individual, either in a single dose or in a series of doses, is effective for treatment or prevention of infection by *S. uberis*. This amount will vary depending upon the health and physical condition of the individual to be treated and on the antigen. It is expected that the amount will fall in a relatively broad range that can be determined by routine trials.

The route of administration of the composition may vary depending on the formulation of the proteins in the composition. The composition may be arranged to be administered intramuscularly, intradermally, subcutaneously, intraperitonealy, intravenously or intramammaryl). Alternatively the composition may be arranged to be administered parenterally, such as by intranasal, oral, buccal, inhalation, epidermal, transcutaneous, topical, vaginal or rectal administration.

The composition may be arranged to be administered as a single dose or as part of a multiple dose schedule. Multiple doses may be administered as a primary immunisation followed by one or more booster immunisations. Suitable timing between priming and boosting immunisations can be routinely determined.

Compositions of the invention may be able to induce a serum bactericidal antibody response after being administered to a subject. These responses are conveniently measured in mice and the results are a standard indicator of vaccine efficacy.

The compositions of the invention may also, or alternatively, be able to elicit an immune response which effects proteins on the host cells to defend against infection by *S. uberis*, without necessarily destroying the bacteria.

According to a further aspect, the present invention provides the use of one or more *S. uberis* sortase-anchored proteins in the preparation of a medicament for eliciting an immune response. The medicament may be used for the prophylactic or therapeutic vaccination of subjects against *S. uberis*. The medicament may be a prophylactic or a therapeutic vaccine.

According a still further aspect, the present invention provides a method of protecting a human or non-human animal, preferably a cow, from the effects of infection by *S. uberis* comprising administering to the human or non-human animal a composition according to any other aspect of the invention.

According to another aspect, the invention provides a method for raising an immune response in a human or non-human animal, preferably a cow, comprising administering a composition according to the invention to the human or non-human animal. The immune response is preferably protective. The method may raise a booster response in a subject that has already been primed. The immune response may be prophylactic or therapeutic.

The uses, methods and compositions of the invention are preferably for the prevention and/or treatment of a disease caused by *S. uberis*.

The skilled man will appreciate that any of the preferable features discussed above can be applied to any of the aspects of the invention.

Preferred embodiments of the present invention will now be described, merely by way of example, with reference to the following figures and examples.

FIGS. 1A, B and C—show the results of bacterial isolation, somatic cell count and clinical response following challenge with wild type *S. uberis* 0140J and a *S. uberis* Srt mutant in dairy cattle. FIG. 1(A) shows the bacterial recovery of *S. uberis* following challenge. Data are represented as the geometric means of the number of bacteria obtained from the milk of animals challenged with either strain 0140J (squares; n=4) or the SrtA mutant (triangles; n=8). FIG. 1 (B) illustrates the inflammatory response following challenge with wild type and Srt mutant of *S. uberis*. Data are represented by the geometric means of the number of somatic cells obtained from the milk of animals challenged with either strain 0140J (squares; n=4) or the SrtA mutant (triangles; n=8). FIG. 1(C) illustrates the combined clinical scores from clinical manifestations following challenge with wild type and Srt mutant of *S. uberis*. Data are represented by the mean of clinical scores given for the appearance of the quarter and appearance of the milk, as outlined in FIG. 2 with either strain 0140J (squares; n=4) or the SrtA mutant (triangles; n=8);

FIG. 2—illustrates in tabular form the manifestation of a clinical response to infection with *Streptococcus uberis*. All quarters and milk samples were analyzed against these criteria at each milking following challenge;

FIG. 3—illustrates in tabular form the proteins found by bioinformatic examination of the *S. uberis* genome that were likely to be anchored by sortase; The genome of *S. uberis* was searched using the LPXXG motif for putative sortase-anchored proteins. The list of proteins identified was refined by using context and position of the motif, ie LPXXG toward the C-terminus and followed by a hydrophobic region and charged residues at a C-terminal position and the presence of a recognisable secretion signal peptide at the N-terminus;

FIG. 4A: lists sortase anchored proteins identified in cell wall extracts of S. uberis 0140J cultured in THB media. [a] Gene and protein annotation according to the genomic sequence of Streptococcus uberis 0140J (Ward et al 2009); [b] Theoretical molecular mass values for protein precursors obtained from Artemis database from the Wellcome Trust Sanger Institute (http://www.sanger.ac.uk/); [c] Number of unique peptide hits for each protein; [d] Percentage of protein sequence covered by experimentally detected peptides; [e] 2 peptides identified in the SrtA mutant cell wall fraction. FIG. 4B: lists sortase anchored proteins identified in cell wall extracts of S. uberis 0140J cultured in BHI media. [a] Gene and protein annotation according to the genomic sequence of Streptococcus uberis 0140J (Ward et al 2009); [b] Theoretical molecular mass values for protein precursors obtained from Artemis database from the Wellcome Trust Sanger Institute (http://www.sanger.ac.uk/); [c] Number of unique peptide hits for each protein; [d] Percentage of protein sequence covered by experimentally detected peptides; [e] 4 peptides identified in the SrtA mutant cell wall fraction;

FIGS. 5A and 5B—shows the identification of Sub1154 and Sub 1370 from extracts of Streptococcus uberis 0140J and srtA mutant. FIG. 5A—rabbit antiserum to Sub1154 was used to probe immunoblots blots of protein detergent extracts from 0140J (lane 2) and SrtA mutant (lane 3), concentrated, precipitated media from 0140J (lane 4), SrtA mutant (lane 5) and Sub1154 mutant (lane 6). Molecular weight standards are shown in lane 1. FIG. 5B-rabbit antiserum to Sub1370 was used to probe immunoblots blots of protein detergent extracts from 0140J (lane 1) and SrtA mutant (lane 2), concentrated, precipitated media from 0140J (lane 3), SrtA mutant (lane 4) and Sub1370 mutant (lane 5). Molecular weight standards are shown in lane 6;

FIGS. 6A to 6O—are the amino acid sequences of S. uberis sortase anchored proteins;

FIG. 6A is the sequence of SUB1370 (Seq ID No: 1) a zinc carboxypeptidase;

FIG. 6B is the sequence of SUB0145 (Seq ID No: 2) a Lactoferrin binding protein;

FIG. 6C is the sequence of SUB0135 (Seq ID No: 3) a frucan beta fructosidase precursor;

FIG. 6D is the sequence of SUB1730 (Seq ID No: 4);

FIG. 6E is the sequence of SUB0888 (Seq ID No: 5);

FIG. 6F is the sequence of SUB0207 (Seq ID No: 6);

FIG. 6G is the sequence of SUB1154 (Seq ID No: 7) a subtilin like serine protease;

FIG. 6H is the sequence of SUB1095 (Seq ID No: 8) a collagen like protein;

FIG. 6I is the sequence of SUB0826 (Seq ID No: 9) a putative surface anchored subtilase;

FIG. 6J is the sequence of SUB0164 (Seq ID No: 10) a putative truncated surface anchored fibronectin binding protein (but is encoded by a probable pseudogene);

FIG. 6K is the sequence of SUB0348 (Seq ID No: 11) a remnant of a putative collagen like protein (but is encoded by a pseudogene);

FIG. 6L is the sequence of SUB1739 (Seq ID No: 12) a putative surface anchored protein (but is encoded by a pseudogene);

FIG. 6M is the sequence of SUB0206 (Seq ID No: 13) a putative exported protein of unknown function;

FIG. 6N is the sequence of SUB0241 (Seq ID No: 14) a putative surface anchored protein of unknown function;

FIG. 6O is the sequence of SUB0337 (Seq ID No: 15) a putative surface located glutamine binding protein;

Figure 1:
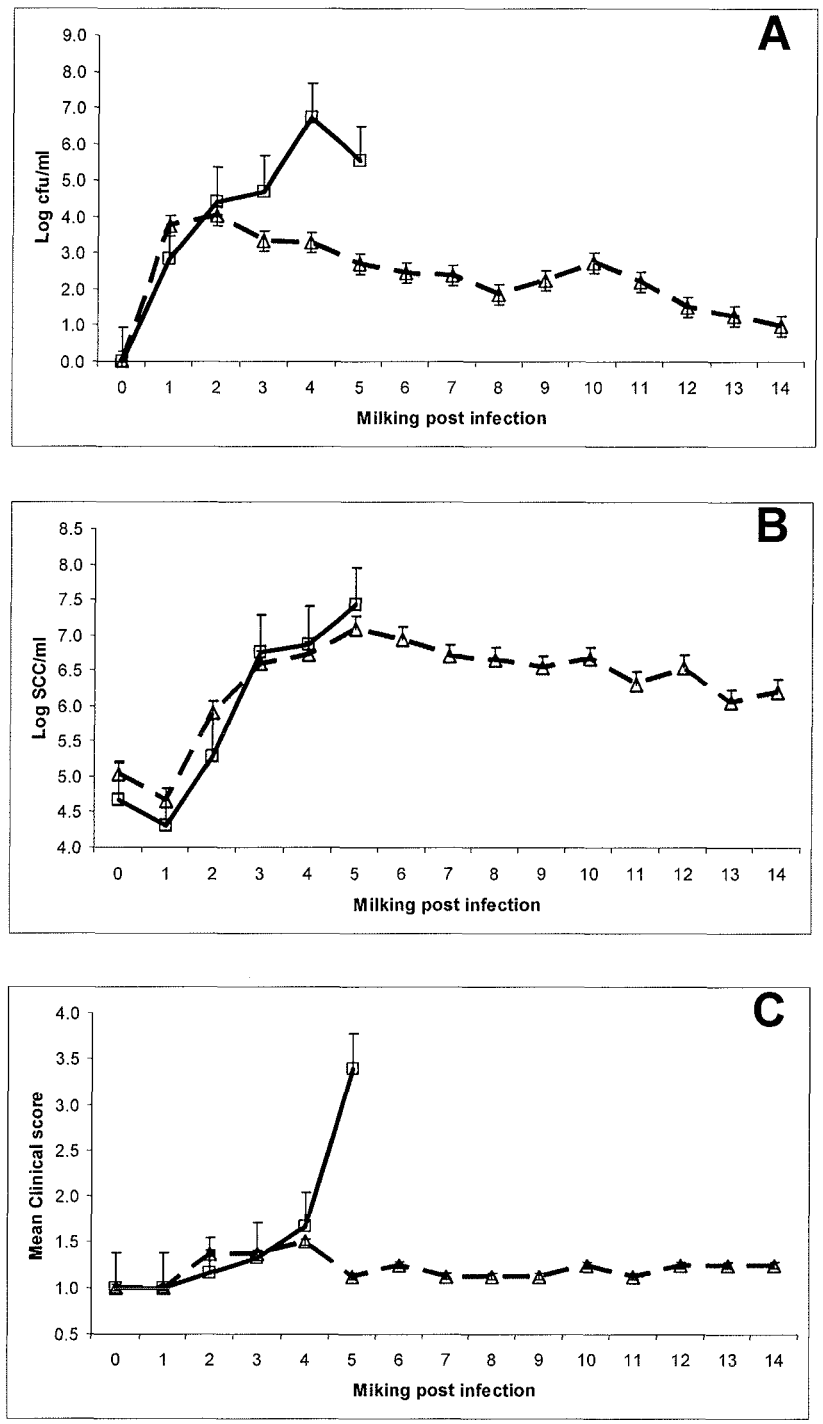

The data presented below demonstrates that proteins anchored to the surface of S. uberis by sortase, a transamidase, are important in virulence and further describes some such proteins (eg sub1095, sub1154 and sub0145) are essential for virulence, and thus are required to be functional in order for this bacterium to cause disease. Proteins are good immunogens. Immune responses to these proteins in the form of antibodies is likely to ablate their function, thus the identified protein would be useful inclusions within immunogenic compositions intended to reduce or prevent infection or diseases caused by S. uberis.

EXAMPLE 1

Production and evaluation of a SrtA mutant of S. uberis

Methods and Materials
Bacterial Strains and Reagents.

Streptococcus uberis strain 0140J, originally isolated from a clinical case of bovine mastitis in the UK, was used throughout this study. The bacterium was routinely grown in Todd Hewitt or Brain Heart Infusion broth.

Skimmed milk was produced from raw bovine milk collected aseptically from several cows from within the dairy herd at the Institute for Animal Health. Milk was collected from animals that were free of intramammary infection. Following centrifugation (3,000×g, 10 min); skimmed milk was removed carefully from the upper fat-layer and the pellet of sedimented cells. The sterility of the skimmed milk was determined by plating 500 µl of milk directly onto blood agar containing aesculin (1.0%, w/v; ABA) and by enrichment culture of 5 ml of milk in and equal volume of Todd Hewitt broth followed by isolation of single colonies on ABA. In both cases, plates were incubated at 37° C. for 18 h. Skimmed milk was stored at 4° C. and used within 72 h.

Other bacterial strains and reagents were used as described in the text.
Isolation of srtA-Mutant by Genotypic Selection.

The srtA (Sub0881) mutant was isolated following PCR screening of a S. uberis 0140J pGhost9::ISS1 mutant bank following a similar protocol to that described previously (Taylor, D. L. et al, 2003. J Bacteriol 185:5210-5219; Ward, P. N. et al 2001 Infect Immun 69:392-399). Briefly, overnight cultures from individual 96-well plates were pooled and genomic DNA was prepared for use as template in PCR amplification reactions containing a locus-specific primer, P261 (srtA) and an ISS1-specific primer, P247 or P250. Amplification was conducted using thirty-five cycles (95° C. for 20 s, 54° C. for 1 min, and 72° C. for 3 min) and was performed with AmpliTaq Gold master mix (ABI). The products were visualized following gel electrophoresis, staining with ethidium bromide and transillumination with UV light. Following plate identification, a well location was similarly identified using genomic DNA pooled from the columns and rows of the target plate. Following isolation of the mutant clone, excision of the plasmid vector was promoted by growth at the permissive temperature (28° C.) without antibiotic selection. Loss of the pGhost9 vector and retention of ISS1 were confirmed by Southern blotting as described previously (Ward, P. N. et al 2001 Infect Immun 69:392-399). Presence of the insertion in srtA was confirmed by PCR amplification of the open reading frame and sequencing of the resulting product across the junction between ISS1 and the disrupted ORF. The PCR primers used are as shown in Table 1 below:

TABLE 1

PCR primers. P247 ISS1 fwd (SEQ ID NO: 16); P250 ISS1 rev (SEQ ID NO: 17); P261 (SEQ ID NO: 18); P409 (SEQ ID NO: 19); P410 (SEQ ID NO: 20); P615 (SEQ ID NO: 21); P630 (SEQ ID NO: 22); P480 (SEQ ID NO: 23); P481 (SEQ ID NO: 24); P621 (SEQ ID NO: 25).

| Designation | Sequence (5'-3') | Application | Template | Annealing temp (° C.) |
|---|---|---|---|---|
| P247 ISS1 fwd | GCTCTTCGGATTTTCGGTATC | ISS1 probe | pGh9::ISS1 | 58 |
| P250 ISS1 rev | CATTTTCCACGAATAGAAGGACTGTC | ISS1 probe | pGh9::ISS1 | 61 |
| P261 | TGGTTGAAGCAGAAGCTGAA | Screening for ISS1 within srtA ORF vs P247 | pGh9::ISS1 | 55 |
| P409 | GAGCAATTGCAAAATGAAAAGC | Amplification of Sub1154 ORF | S. uberis 0140J genomic DNA | 58 |
| P410 | ATGTCAAAAGCCCGGTACCTTTACAG | Amplification of Sub1154 ORF | S. uberis 0140J genomic DNA | 58 |
| P615 | GAAATGATGATGAGAAATTGAGA | Screening for ISS1 within Sub1154 ORF vs P247 | S. uberis 0140J ::pGhost9-ISS1 genomic DNA pools | 57 |
| P630 | AGCCACAAACACCATTCACA | Screening for ISS1 within Sub1154 ORF vs P247 | S. uberis 0140J ::pGhost9-ISS1 genomic DNA pools | 59 |
| P480 | GAAGAAGTGGTAACTGCTACAAAC | Amplification of Sub1370 ORF | S. uberis 0140J genomic DNA | 60 |
| P481 | TACTAACTTCTTGTCATCTTGGTACCTTTT | Amplification of Sub1370 ORF Screening for ISS1 within Sub1370 ORF | S. uberis 0140J genomic DNA | 64 |
| P621 | CAACGAATCAACAAACTGAAAGC-3' | Screening for ISS1 within Sub1370 vs P250 | S. uberis 0140J ::pGhost9-ISS1 genomic DNA pools | 59 |

Extraction of Chromosomal DNA from *S. Uberis*

Genomic DNA was prepared using a variation of the method of Hill and Leigh as described previously (Hill, A. W. et al 1994 FEMS Immunol Med Microbiol 8:109-117). Briefly, 1.5 ml of an overnight culture was centrifuged at 10,000×g for 2 minutes and the cell pellet washed with 500 μl of 10 mM Tris-Cl, 5 mM EDTA, pH 7.8. Bacterial cell walls were disrupted by resuspension in 375 μl of 10 mM Tris-Cl, 5 mM EDTA pH 7.8 containing 30 units/ml mutanolysin and 10 mg/ml lysozyme (both from Sigma-Aldrich, St Louis, Mo., USA) and subsequent incubation at 37° C. for 30 minutes. Total cell lysis was achieved by addition of 20 μl of SDS solution (20% w/v in 50 mM Tris-Cl, 20 mM EDTA, pH 7.8) and Proteinase K (Sigma) to a final concentration of 150 μg/ml and a further incubation at 37° C. for 1 h. Cell wall material was removed by precipitation following the addition of 200 μl of saturated NaCl and subsequent centrifugation at 12,000×g for 10 minutes. The supernatant was extracted with phenol chloroform and DNA precipitated by addition of 2 volumes of absolute ethanol. DNA pellets were washed with 70% aqueous ethanol and air-dried prior to resuspension in TE buffer containing 20 μg/ml RNAase-A (Sigma).

Challenge of Lactating Dairy Cows with S. uberis 0140J and SrtA Mutant

The role of SrtA in the pathogenesis of infection was determined by comparison of the virulence of strain 0140J and the mutant lacking SrtA (srtA mutant) in an intramammary infection model in the dairy cow. Bacteria were grown for 18 h at 37° C. in Todd Hewitt broth. Cells were recovered by centrifugation (10,000×g, 10 min), suspended in pyrogen-free saline (Sigma) and diluted in the same to provide the required cell density. Suspensions of each strain were held on ice prior to being used to challenge animals. The number of viable bacteria in identical aliquots of each suspension was enumerated both prior to and following challenge.

Six dairy cows, 2-10 weeks into their first lactation, were selected from the Institute's dairy herd for challenge. Criteria for selection were: absence of signs of mastitis, absence of bacteria in milk samples prior to challenge, no history of mastitis during the current lactation and no evidence of intramammary infection in milk samples taken at 7 and 14 days after parturition. Animals were challenged in mammary quarters by infusion of 1 ml of pyrogen-free saline (Sigma) containing S. uberis. Two animals were challenged in a total of four quarters with $6.0 \times 10^2$ cfu of strain 0140J and a further four animals, were challenged in a total of eight quarters with a similar dose of the srtA mutant. Following challenge, animals were milked and inspected twice daily (07:00 h and 15:30 h) and those in which predetermined criteria for clinical end points (clotted and discoloured milk and/or udder quarter swollen or causing discomfort on palpation) had been reached were treated with proprietary branded antibiotics in line with the prescribed criteria outlined in FIG. 2. Milk samples were taken and analysed for bacteria and somatic cells, as described below.

Analysis of Milk Samples

The number of viable bacteria present was estimated by direct plating of 1 ml and 100 µl of each milk sample on to ABA. Samples were also diluted in saline and 50 µl of each dilution plated directly onto ABA. In each case, the presence and/or number of S. uberis was determined and the genotype of the recovered isolates was determined by comparing restriction fragment length polymorphism (RFLP) of chromosomal DNA and amplification of the srtA locus, as described below. The number of somatic cells present in milk samples was determined using a coulter counter (Beckman Coulter, Ltd).

Preparation of Proteins from Bacterial Growth Media by Methanol Chloroform Precipitation Bacteria were grown in BHI (200 ml) with cultures grown to an approximate OD600 nm of 0.5 and harvested by centrifugation (16,000×g, 20 min, 4° C.) and bacterial growth media was filter sterilised through a 0.22 µM filter (Millipore). After the addition of complete protease inhibitor (Roche) at a 1× concentration, the bacterial growth media was concentrated approximately 100-fold using Amicon centrifugal filter devices (Millipore) with a molecular weight exclusion of 10 kDa. To precipitate proteins, 600 µl of methanol and 150 µl of chloroform (both from BDH) was added to 200 µl of concentrated bacterial growth media. The preparation was vortexed and 450 µl of MilliQ water was added prior to centrifugation (16,000×g, 1 min). The upper phase was carefully removed and discarded and 450 µl of methanol was added to the remaining material which was vortexed and centrifuged (16,000×g, 2 min). The supernatant was discarded and the remaining pellet air-dried before resuspension in SDS-loading buffer.

Extraction of Non-Anchored Proteins with Detergent

The bacterial pellets from the above cultures were washed 3 times in 40 ml of PBS and resuspended in 500 µl of PBS containing hyaluronidase (100 U/ml, Sigma-Aldrich). Cells were incubated for 2 hours at 37° C. and the hydrolysed capsular material removed by centrifugation (8000×g, 6 min, 4° C.). Cells were washed 3 times in 40 ml of PBS and resuspended in 200 µl of 0.1% (v/v) Nonldet P-40 (NP-40) in PBS. The detergent extract was harvested following removal of the bacterial cells by centrifugation (16,000×g, 10 min, 4° C.).

Production and Purification of Recombinant Sub1154 and Sub 1370 Proteins

Primers p409 and p410 (see table above) were designed to amplify from S. uberis 0140J genomic DNA the predicted mature coding sequence (ie lacking N-terminal signal sequence) of Sub1154, a putative srtA substrate with homology to subtilase-like serine protease. A 3.4 kb amplicon was generated using Phusion™ high fidelity polymerase (New England Biolabs), purified using a MinElute PCR Purification Kit (Qiagen) and treated with KpnI (New England Biolabs) to facilitate directional cloning. Plasmid pQE1 (Qiagen) was prepared using PvuII, KpnI and Antarctic phosphatase (all from New England Biolabs) and the construct ligated (T4 DNA Ligase, New England Biolabs) overnight at 20° C. according to the manufacturers' instructions. Twenty microliters of the ligation mixture was desalted using the method of Atrazhev and Elliott (Atrazhev, A. M., and J. F. Elliott. 1996 Biotechniques 21:1024). Approximately 10 ng of the desalted ligation mixture was transformed into Escherichia coli M15 pREP4 (Qiagen) and recombinant clones selected on LB Kan25 µg/ml Amp50 µg/ml agar plates. Recombinant (6×His-tagged) Sub1154 protein commencing at residue Asp34 was purified by dilution (1/30) of overnight culture into 1600 ml LB broth containing 50 µg/ml of ampicillin and 25 µg/ml of kanamycin and growth at 20° C. without shaking for 2 h. Recombinant Sub1370 was similarly prepared, but using the primers P480 and P481, and was grown similarly in 800 ml of culture medium. Protein expression was induced by addition of IPTG to a final concentration of 0.2 mM. Cultures were incubated for a further 2-4 hrs and then centrifuged at 8,000×g for 20 min to harvest the bacterial cells. Approximately 1 mg and 0.3 mg of soluble 6× His tagged Sub1154 and Sub1370 proteins respectively was purified in the presence of protease inhibitors (Complete-EDTA free; Roche) using CelLytic and HisSelect high flow cartridges (both from Sigma) according to the manufacturers' instructions.

Production of Sub1154 and Sub1370 Antiserum in Rabbits and Immuno-Blotting

Five aliquots of approximately 50 µg freeze dried purified recombinant Sub1154 and Sub1370 proteins were supplied to Davids Biotechnologie (Germany) for serum production in rabbits. Anti-serum (50 ml) was supplied filter sterilised and containing 0.02% sodium azide as a preservative.

Detergent and media extracts from cultures of wild type S. uberis and a SrtA mutant were separated on 10% sodium-dodecyl sulphate polyacrylamide (SDS-PAGE) gels and then transferred onto nitrocellulose membranes (Amersham) for immuno-detection, or alternately Coomassie stained using InstantBlue (Novexin). Transfer was performed at 170 mA for 1 hr in a (Biorad) Transblot apparatus in transfer buffer consisting of 25 mM Tris-base, 192 mM glycine and 20% (v/v) methanol, pH 8.1-8.4. Following transfer, membranes were incubated in a blocking solution of 1% skim milk powder in PBS at 4° C. overnight. Membranes were washed three times for 5 min in PBS containing 0.1% Tween 20 (PBST)

then incubated with rabbit antisera at 1/12,000 dilution for the Sub1154 antiserum and 1/16,000 dilution for the Sub1370 antiserum in blocking solution for 1 hour. Membranes were washed three times for 5 min in PBST then incubated with goat anti-rabbit immunoglobulin G conjugated to HRP at a 1/1,000 dilution (Southern Biotech) for 1 hour. Membranes were washed again as above and HRP conjugate detected using a solution of 4-chloronaphthol (0.5 mg/ml) in PBS containing 16.7% methanol and 0.00015% (v/v) of $H_2O_2$, incubated for 1 hour in the dark, before membranes were washed in PBS and allowed to dry.

Isolation and Genetic Characterization of srtA Mutant

Analysis of the complete genome of S. uberis 0140J confirmed the presence of a single sortase homologue, sortase A (srtA) (Ward, P. N. et al (submitted 2008) BMC Genomics). A mutant clone was isolated with the ISS1 element inserted between base pairs 248 and 249 of, and in reverse orientation to, the sortase coding sequence. The translation product of this mutated srtA gene consisted of the first 82 residues of the 252 amino acids encoded in the srtA ORF together with a further 18 residues in the ISS1 element before a stop codon was reached.

Infectivity and Virulence of the Wild-Type and srtA Mutant S. Uberis Following Experimental Challenge in the Bovine Mammary Gland.

The infectivity and virulence of the srtA mutant, compared to a wild type strain, was determined by challenging the bovine mammary gland of a number of diary cows. All challenged quarters of animals that received 600 cfu of wild type S. uberis became infected and shed bacteria at around $10^6$ to $10^7$ cfu/ml by 48-60 h post challenge (FIG. 1A). Following challenge of eight quarters on four animals with a similar dose of the srtA mutant, all showed evidence of infection and the srtA mutant was detected in milk at levels similar to those for the wild type for up to 24 h post challenge. However, subsequent bacterial colonization declined, from a maximum of $10^4$ cfu/ml of milk by 24 h post challenge, such that by the end of the experiment (7 days post challenge) the mean bacterial number present was around 10 cfu/ml (FIG. 1B). By this time only two of the eight quarters continued to shed bacteria, the remainder having eliminated the infection (<1 cfu/ml milk).

The cellular infiltration into the mammary gland in response to infection was identical in both groups of animals and was not dependant on the challenge strain. In each case, this was similar to that reported previously in this model and reached a maximum of approximately $10^7$ cells/ml of milk by 48-60 h post challenge. In animals challenged with the wild type strain this coincided with the appearance of acute clinical signs of mastitis (FIG. 2 and FIG. 1C) which required administration of antibiotic therapy to eliminate infection and to alleviate signs of disease. In stark contrast, animals that had received the srtA mutant showed little, if any, signs of mastitis (FIG. 2 and FIG. 1C).

The results presented in FIG. 1 demonstrate that S. uberis requires the sortase protein, encoded by srtA, for the full expression of virulence by this bacterium. Although initially able to colonise the bovine mammary gland similarly to the wild-type S. uberis, the mutant lacking SrtA was unable to colonise the gland to high levels; with bacterial maximal numbers remaining approximately 1000-fold lower than those detected in milk from animals challenged with the wild type strain. This corresponded with the failure of the srtA mutant to induce progressive clinical signs of disease.

It is understood that srtA anchors one or more proteins to the surface of the bacterium that are responsible for virulence, that is for high level colonisation and/or induction of severe inflammatory reactions associated with clinical disease.

Detection of Sortase Anchored Proteins in S. Uberis

To identify proteins anchored to the cell wall of S. uberis by sortase, the cell wall proteins of wild type S. uberis were compared to those of a SrtA mutant of S. uberis.

The methodology used to isolate tryptic peptides of anchored cell wall proteins is as follows. Bacterial cultures were grown in either THB or BHI to both exponential and stationary phases of growth. Exponential cultures were grown in 1.5 liters of broth to an optical density of 0.6 at OD550 nm whilst stationary phase cultures were grown in 1 liter of broth overnight. Bacterial cell pellets were harvested by centrifugation (16,000×g, 10 min, 4° C.) and consecutively washed with PBS, 0.1% (v/v) Nonidet P40 (NP40) in PBS, and PBS and harvested by centrifugation as above. Cell pellets were resuspended in PBS containing 1× Complete protease inhibitors (Roche) and disrupted by bead beating in screw capped microfuge tubes containing 0.1 mm zirconia/silica beads at 5×1 min intervals at maximum speed, with interspersed resting periods on ice. Unbroken cells and beads were removed by centrifugation twice (8,000×g, 10 min, 4° C.) and supernatants then subjected to high speed centrifugation (125,000×g, 30 min). The resulting pellets were resuspended in 4% SDS/PBS and heated at 80° C. for 4 hours, then centrifuged (200,000×g 30 min). Resulting pellets were washed 4 times with MilliQ water at 30° C. and centrifuged as above. Pellets were then resuspended in 50 mM ammonium bicarbonate containing 1 µg of proteomics grade trypsin (Sigma) and incubated shaking overnight at 37° C. Peptides were harvested from the supernatant following centrifugation (16,000×g, 10 min) and digestion was stopped by the addition of formic acid at a final concentration of 0.1%.

Peptides were separated and analysed by nanoLC-MS/MS using a reverse-phase liquid chromatography system. The interpretation and presentation of MS/MS data was performed according to published guidelines, with searches performed using Mascot software (Matrixscience, London, UK) using a genomic database generated for S. uberis 0140J.

The sequences of the tryptic peptides were aligned with the translated genomic sequence of Streptococcus uberis to identify the proteins present The nine proteins listed in FIGS. 4 and B were found to be present on cell walls prepared from S. uberis 0140J, but were absent from equivalent preparations made from cultures of the isogenic srtA deficient mutant of S. uberis, demonstrating the proteins to be sortase-anchored proteins.

The sequence of the nine sortase anchored proteins are given in FIGS. 6A to 6I. FIGS. 6J to 6O are the sequences of the putative sortase anchored proteins identified by proteomics.

Detection of Sub1154 and Sub1370 Protein in Wild Type and Srt A Mutant S. uberis Protein Extracts Recombinant Sub1154 and recombinant Sub1370, two examples of S. uberis sortase-anchored proteins, were both generated from amplified genomic S. uberis DNA and the product cloned in E. coli using the pQE1 vector, which incorporated a 6×His tag at the N-terminal of each protein. The recombinant protein was purified utilizing the 6×His tag and used for the production of anti-sera.

Figure 5:
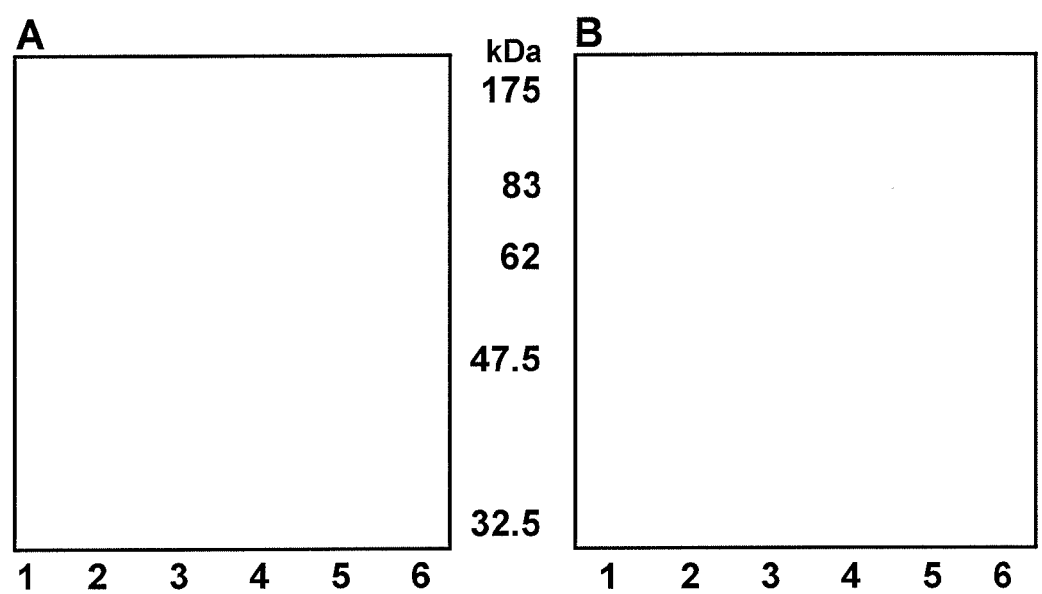

Rabbit anti-Sub1154 and anti-Sub1370 were then used to detect the Sub1154 and Sub1370 proteins by immunoblotting of detergent and media extracts of S. uberis 0140J and the srtA mutant. Media extracts from Sub1154 and Sub1370 mutants grown in BHI were also probed with the antisera. Detection of Sub1154 was confirmed in the srtA detergent extract, and also in the Sub1154 mutant media extract. In the latter case the predicted truncated form of the protein was detected (FIG. 5A). The protein corresponding to Sub1370 was detected only in the growth media obtained from the srtA mutant (FIG. 5B). The presence of the Sub1154 and Sub1370 proteins only in extracts from the srtA mutant indicate that in the wild type strain the proteins are anchored to the cell wall of S. uberis by sortase.

EXAMPLE 2

Investigation into the Requirement for Specific Sortase Anchored Proteins for Virulence of S. Uberis Following on from the identification of sortase anchored proteins, each of the genes encoding these was mutated within the wild type strain. The mutants, each lacking an individual sortase anchored protein, were used in a challenge model in dairy cattle to assess virulence. The proteins missing from those that show reduced or ablated virulence are involved in pathogenesis/pathology of disease. Induction of a neutralizing immune (antibody) response to any and preferably all of these proteins would result in less disease following infection with wild type strains. Thus vaccines containing any or all of those identified as having a role in virulence would be useful in the prevention of mastitis in cattle.

Methodology

Production and Isolation of Mutant Strains of S. Uberis Lacking SrtA Anchored Proteins (Sub 0135, Sub 0145, Sub0207, Sub0241, Sub 0826, Sub0888, Sub1095, Sub1154, Sub1370, Sub1730)

Insertionally inactivated mutants were located within a random insertional mutant bank by PCR screening of a S. uberis 0140J pGhost9::ISS1 mutant bank following a similar protocol to that described previously (Taylor, D. L. et al, 2003. J Bacteriol 185:5210-5219; Ward, P. N. et al 2001 Infect Immun 69:392-399). Briefly, overnight cultures from individual 96-well plates were pooled and genomic DNA was prepared for use as template in PCR amplification reactions containing a locus-specific primer for each gene of interest and used in conjunction with primer specific to ISS1. Following isolation of the mutant clone, excision of the plasmid vector was promoted by growth at the permissive temperature (28° C.) without antibiotic selection. Loss of the pGhost9 vector and retention of ISS1 were confirmed by Southern blotting as described previously (Ward, P. N. et al 2001 Infect Immun 69:392-399). Presence of the insertion in the appropriate ORF was confirmed by PCR amplification of the open reading frame and sequencing of the resulting product across the junction between ISS1 and the disrupted ORF.

Attempts to isolate an insertion mutant from the 0140J random mutant bank with ISS1 located appropriately near to the start of the SUB1154 coding sequence proved unsuccessful. A targeted deletion strategy was used to ablate production of the SUB1154 gene product. Briefly, two fragments located at either end of the 3432 base pair open reading frame were amplified from genomic DNA. The two fragments were purified and then used as template in equal proportion in a further PCR amplification reaction to generate a single Δ1154 product lacking 3169 base pairs from the 3432 base pair SUB1154 coding sequence. This amplicon was subcloned into the multiple cloning site of the low copy pG+h9 temperature sensitive plasmid. The plasmid construct was amplified by transformation of E. coli TG1 RepA with selection on 200 μg/μl Erythromycin at 37.5° C. and 10 ng of the subsequently purified plasmid used to further transform S. uberis 0140J with selection on 1 μg/ml Erythromycin at 28° C. S. uberis 0140J/pG+ h9::Δ1154 transformants were grown to $OD_{550}$ 0.5 in Todd Hewitt broth culture at 28° C., the growth temperature was then raised to the non-permissive plasmid replication temperature of 37.5° C. to force single cross-over chromosomal integration. Integrants were selected on THA containing Ery at 1 μg/ml at 37° C. and subsequently grown in THB lacking antibiotic at 28° C. to promote excision of the pG+h9 replicon by a second cross-over event. Resulting bacteria were plated on to THA and colonies picked following overnight growth at 37° C. Deletion of the Sub1154 locus was determined by PCR amplification of the Sub1154 locus.

Challenge of Lactating Dairy Cows with S. Uberis

The requirement for individual SrtA substrates for virulence was determined by experimental challenge in a well established intramammary infection model in the dairy cow. Bacteria were grown for 18 h at 37° C. in Todd Hewitt broth. Cells were recovered by centrifugation (10,000×g, 10 min), suspended in pyrogen-free saline (Sigma) and diluted in the same to provide the required cell density (500-1500 cfu/ml). Suspensions of each strain were held on ice prior to being used to challenge animals. The number of viable bacteria in identical aliquots of each suspension was enumerated both prior to and following challenge.

Dairy cows, 2-10 weeks into their first lactation, were selected for challenge. Criteria for selection were: absence of signs of mastitis, absence of bacteria in milk samples prior to challenge, no history of mastitis during the current lactation and no evidence of intramammary infection with S. uberis in milk samples taken at 7 and 14 days after parturition. Animals were challenged in mammary quarters by infusion of 1 ml of pyrogen-free saline (Sigma) containing between 500-1500 cfu of S. uberis.

Following challenge, animals were milked and inspected twice daily (07:00 h and 15:30 h) for a period of 4 days. Those in which predetermined criteria for clinical end points (clotted and discoloured milk and/or udder quarter swollen or causing discomfort on palpation) had been reached were treated with proprietary branded antibiotics. Milk samples were taken at each milking and analysed for the presence of bacteria and somatic cells, as described below.

Analysis of Milk Samples

The number of viable bacteria present was estimated by direct plating of 50 μl of each milk sample on to ABA. Samples were also diluted in saline and 50 μl of each dilution plated directly onto ABA. In each case, the presence and/or number of S. uberis was determined and the genotype of the recovered isolates was determined by amplification of the appropriate locus. The number of somatic cells present in milk samples was determined using DeLaval portable cell counter according to the manufactures instructions.

Results

Figure 7:
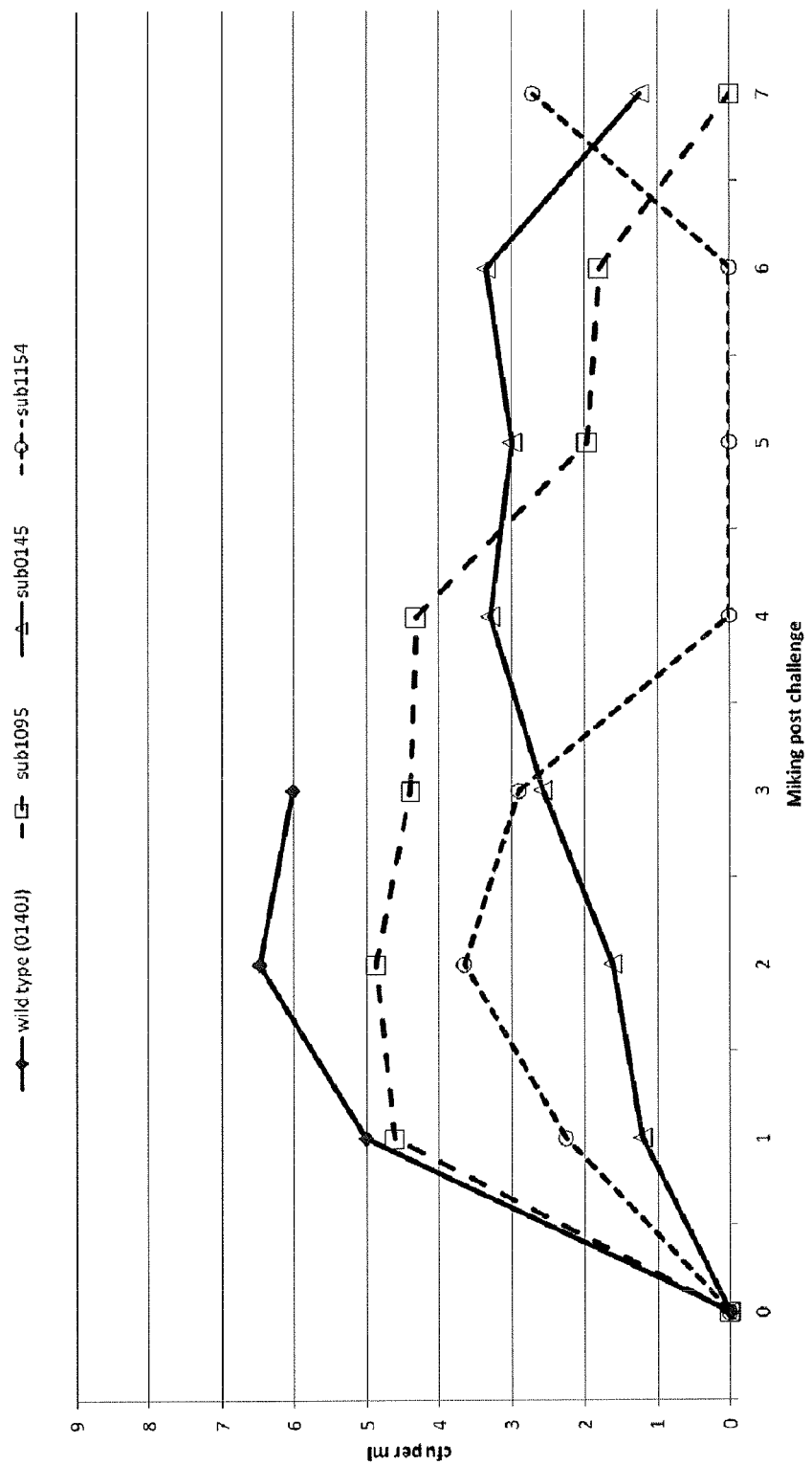
FIG. 7 shows the bacterial colonisation following challenge with wild type (0140J) and attenuated mutant strains lacking sub0145, sub1095 or sub1154. Data is expressed as geometric means of $Log_{10}$ cfu/ml detected in milk samples obtained at each milking after experimental challenge.

Mutants lacking one of Sub 0145, Sub1095, or Sub1154 were used to challenge mammary quarters to determine if the mutation had resulted in major attenuation of S. uberis. In all cases, the strains were recovered from milk post challenge and each was genotyped to show the presence of the correctly mutated gene. challenge with strains (lacking either sub1095, sub0145 or sub1154) resulted in relatively poor colonisation for the duration of the experiment (FIG. 7) and in contrast to the wild type strain, in no instance was any of these strains able to induce clinical signs of disease. Consequently, the function of these proteins in pathogenesis of infection can be considered essential and non-redundant. Induction of a neutralizing immune (antibody) response to any and preferably all of these proteins would be predicted to result in less disease following infection with wild type strains.

I claim:

1. An immunogenic composition comprising one or more of the Streptococcus uberis proteins selected from the group consisting of SUB1154, SUB1095, and SUB0145, wherein the composition is capable of eliciting an immune response, when administered to a subject.

2. The immunogenic composition of claim 1, wherein the immunogenic composition comprises two or more of the Streptococcus uberis proteins selected from the group consisting of SUB1154, SUB1095, and SUB0145.

3. The immunogenic composition of claim 2, wherein the composition comprises the Streptococcus uberis proteins SUB1095 and SUB1154.

4. The immunogenic composition of claim 1, wherein the subject is a mammal, optionally a ruminant.

5. The immunogenic composition of claim 1, wherein the antigenic composition is capable of eliciting an immune response directed to an antigen in the composition and acts to prevent or reduce infection by Streptococcus uberis in a subject to whom the immunogenic composition has been administered.

6. The immunogenic composition of claim 1, wherein the composition comprises a further one or more antigens, in addition to one or more S. uberis proteins.

7. The immunogenic composition of claim 1, wherein the composition is used to elicit/produce a protective immune response when administered to a subject.

8. The immunogenic composition of claim 1, wherein the composition is used as a prophylactic or a therapeutic vaccine against S. uberis.

9. The immunogenic composition of claim 1, wherein the composition further comprises an adjuvant.

10. The immunogenic composition of claim 1, wherein the composition is used as a vaccine against infections caused by S. uberis.

11. The immunogenic composition of claim 8, wherein the vaccine is administered prophylactically to animals at risk of exposure to S. uberis, and/or therapeutically to animals who have already been exposed to S. uberis.

12. The immunogenic composition of claim 8, wherein the composition comprises an immunologically effective amount of antigen comprised of S. uberis proteins.

13. A pharmaceutical composition comprising one or more S. uberis proteins selected from the group consisting of SUB1154, SUB1095, and SUB0145 in combination with a pharmaceutically acceptable carrier or excipient.

14. The composition of claim 1 for use for the prevention and/or treatment of a disease caused by S. uberis.

15. A method of protecting a human or non-human animal from the effects of infection by S. uberis comprising administering to the human or non-human animal a therapeutically effective amount of a composition according to claim 1.

16. A method for raising an immune response in a human or non-human animal comprising administering an immunologically effective amount of a composition according to claim 1 to the human or non-human animal.

* * * * *

SEQUENCE LISTING

<160> NUMBER OF SEQ ID NOS: 25

<210> SEQ ID NO 1
<211> LENGTH: 1073
<212> TYPE: PRT
<213> ORGANISM: Streptococcus uberis

<400> SEQUENCE: 1

```
Met Thr Lys Asn Arg Ser Ser His Ser Thr Tyr Ala Asp Lys Val Ile
1               5                   10                  15

Lys Gly Leu Ser Ala Ser Cys Phe Ile Leu Gly Ala Phe Val Phe Ala
            20                  25                  30

Gln Gln Val Ser Ala Glu Glu Val Thr Ala Thr Asn Thr Ser Leu
        35                  40                  45

Thr Ala Pro Thr Val Thr Thr Val Ser Pro Leu Thr Asn Thr Asp Val
        50                  55                  60

Ser Ala Thr Ala Val Ala Ala Asp Ser Ile Ala Ser Pro Val Thr Thr
65                  70                  75                  80

Thr Asp Ser Asn Leu Asn Ser Ala Pro Ile Ile Asp Thr Ser Asn Pro
                85                  90                  95

Ser Asn Ile Thr Ser Pro Thr Asp Thr Asn Thr Ser Thr Thr Ser Ser
            100                 105                 110

Asp Thr Thr Ser Ser Pro Ile Pro Val Thr Leu Asn Lys Ala Ala Ile
        115                 120                 125

Ala Ser Pro Thr Ser Gln Thr Glu Thr Leu Ala Ser Gln Glu Ile Tyr
    130                 135                 140

Met Asp Lys Val Asn Gln Val Thr Ile Asn Thr Thr Val Asn Pro Ala
145                 150                 155                 160

Thr Pro Met Thr Trp Thr Ile Glu Asn Tyr Pro Asn Gln Thr Tyr Asn
                165                 170                 175

Met Gln Thr Gly Asp Phe Thr Gly Ser Pro Ser Tyr Thr Val Thr Ser
            180                 185                 190

Thr Ser Pro Asn Asn Ser Ser Val Gln Ile Glu Ile Pro Pro Leu Phe
        195                 200                 205

Gly Thr Asp Leu Ser Leu Arg Trp Pro Asn Asn Ile Arg Arg Thr Tyr
    210                 215                 220

Arg Asp Tyr Met Gly Ser Tyr Thr Leu Lys Gly Ile Ser Glu Asp Gly
225                 230                 235                 240

Leu Thr Ile Val Thr Lys Glu Leu Ile Leu Arg Pro Tyr Ala Asp Tyr
                245                 250                 255

Met Thr His Glu Glu Leu Leu Asn Glu Leu Asn Ala Ile Glu Ala Asn
            260                 265                 270

His Ala Thr Asp Arg Leu Val Thr Ile Glu Thr Ile Gly Gln Ser Ala
        275                 280                 285

Leu Gly Asn Ala Ile Lys Met Gly Ile Val Ala Lys Asp Gln Ala Ser
    290                 295                 300

Leu Asp Thr Tyr Leu Asn Gln Thr Thr Pro Met Met Leu Met Asp Pro
305                 310                 315                 320

Asp Gln Ala Leu Asn Leu Leu Ala Gln Gly Lys Phe Asp Tyr Lys Leu
                325                 330                 335

Pro Ile Leu Ile Asn Asn Thr His Ala Asp Glu Gln Pro Gly Ile Asp
            340                 345                 350

Val Val Arg Gly Leu Phe Lys Thr Phe Ala Thr Glu Ser Val Ile Asn
        355                 360                 365
```

```
Tyr Gln Thr Val Asp Ala Ala Asn Asn Pro Thr Thr Val Gln Ile Asp
    370                 375                 380

Ile Lys Ala Leu Leu Asp Lys Val Ile Leu Leu Phe Asn Phe Thr Glu
385                 390                 395                 400

Asn Pro Asp Gly Asp Ile Ala Asn Thr Arg Ala Leu Asn Asn Gly Leu
                405                 410                 415

Asp Pro Asn Arg Asp Thr Gly Tyr Gln Thr Asn Pro Glu Thr Arg Ala
            420                 425                 430

Ile Val Glu Gln Ile Asn Lys Trp Asn Pro Ile Ser Ile Phe Asp Val
        435                 440                 445

His Gly Phe Val Lys Glu Phe Leu Ile Glu Pro Cys Thr Pro Pro His
    450                 455                 460

Asp Pro Asn Phe Glu Tyr Asp Leu Phe Asp Ala Ser Leu Val Glu Gly
465                 470                 475                 480

Ala Arg Glu Met Gly Asn Ala Gly Ile Thr Asn Ser Val Tyr Asp Ser
                485                 490                 495

Tyr Ile Ile Pro Lys Phe Asp Tyr Gly Ser Gly Trp Asp Ser Phe
            500                 505                 510

Ser Gly Tyr Thr Ala Val Tyr Gly Leu Tyr Gln Gly Ile Leu Gly His
        515                 520                 525

Thr Ile Glu Ile Pro Glu Thr Asn Gln Glu Ser Tyr Asn Ala Gly Tyr
    530                 535                 540

Phe Ala Val Leu Ala Gly Ile Asn Tyr Asp Leu Ala Asn Ser Asp Gln
545                 550                 555                 560

Leu Met Lys Asn Lys Leu Thr Phe Phe Ser Arg Gly Ile His Lys Ala
                565                 570                 575

Glu Val Ala Ala Ala Glu Glu Ala Leu Leu Thr Val Asp Gly Ser Val
            580                 585                 590

Lys Gly Arg Ile Lys Asp Gly His Asp Thr Phe Phe Pro Asp Tyr Tyr
        595                 600                 605

Met Ile Pro Met Thr Leu Ser Thr Glu Ser Asp Thr Asp Gln Ala Phe
    610                 615                 620

Lys Met Ile Asp Tyr Phe Arg Arg Asn Gly Val Ile Leu Asn Glu Leu
625                 630                 635                 640

Thr Ala Asp Val Ala Gly Tyr His Lys Gly Asp Leu Val Ile Asp Met
                645                 650                 655

Ala Gln Ala Lys Arg Gly Phe Ala Asn His Val Leu Tyr Lys Gly Ala
            660                 665                 670

Asn Glu Ser Glu Trp Pro Ala Met Tyr Ala Glu Leu Val Met Asn Phe
        675                 680                 685

Pro Ala Met Arg Gly Phe Lys Ala Asp Ala Ile Tyr Ala Asp Ser Leu
    690                 695                 700

Phe Ala Gly Asn Leu Gly Ala Val Thr Leu Thr Ser Ala Pro Arg Thr
705                 710                 715                 720

Ala Pro Ser Asp Lys Glu Tyr Tyr Ile Val Ser Asn Asn Ser Leu Ala
                725                 730                 735

Ala Val Gln Ala Val Asn Ala Ala Ile Arg Ala Gly Lys Asn Val Tyr
            740                 745                 750

Leu Thr Asn Asp Gly Tyr Val Met Asp Lys Ala Thr Tyr Glu Ser Val
        755                 760                 765

Ile Gly Thr Tyr Pro Leu Phe Ala Gln Ala Thr Cys Met Lys Pro Val
    770                 775                 780

Gly Asp Thr Leu Lys Ala Ile Lys Val Tyr Ala Pro Gly Asn Pro Asn
785                 790                 795                 800
```

-continued

```
Leu Tyr Leu Gly Phe Asn Ser Pro Ser Glu Val Ser Leu Ala Leu Asn
            805                 810                 815

Gln Met Gly Phe Asp Val Val Pro Ser Val Gln Ala Asp Val Ile
        820                 825                 830

Val Leu Asp Asn Asp Gln Phe Asp Ala Ser Ile Leu Gly Lys Lys Pro
        835                 840                 845

Val Ile Ile Leu Gly Gly Ser Ala Met Ala Lys Leu Glu Ser Leu Gly
        850                 855                 860

Ile Leu Thr Gly Phe Asp Ala Ala Met Thr Ser Glu Ser Asp Gly Ser
865                 870                 875                 880

Ser Tyr Glu Gly Leu Met Lys Ile Ser Leu Asp Ala Asn Ser Pro Tyr
                885                 890                 895

Thr Ser Gly Tyr Ala Ala Asn Ser Leu Tyr Tyr Ser Asn Ser Gly Ser
                900                 905                 910

Trp Ile Glu Gly Val Pro Thr Gly Phe Met Thr Leu Ala Asn Ile Ser
        915                 920                 925

Ala Ser Asp Phe Tyr Val Ser Gly Trp Trp Pro Asn His Glu Gly Leu
        930                 935                 940

Ala Asn Lys Thr Val Ala Ile Ser Gly Leu Tyr Gln Gly Gln Pro Met
945                 950                 955                 960

Phe Ile Phe Ala Gly Asn Pro Val Asn Lys Thr His Thr Ile Asn Phe
                965                 970                 975

Tyr Arg Trp Val Ser Asn Ala Ile Phe Gly Thr Asn Leu Thr Ser Phe
                980                 985                 990

Ile Glu Gly Gln Cys Thr Ile Pro Thr Asp Ser Glu Thr Gln Val Val
        995                 1000                1005

Arg Val Asn His Asn Gly Gln Thr Val Ala Val Tyr Gln Gln Val
    1010                1015                1020

Ala Asn Lys Glu Val Asn Gly Thr Val Ser Gln Asn Ser Leu Pro
    1025                1030                1035

Ala Leu Ala Asp Gly Ser His Lys Asp Asp Ser Lys Leu Phe Trp
    1040                1045                1050

Val Thr Gly Leu Leu Val Ala Ser Gly Gly Leu Phe Ala Ala Leu
    1055                1060                1065

Lys Arg Arg Glu Asp
    1070

<210> SEQ ID NO 2
<211> LENGTH: 515
<212> TYPE: PRT
<213> ORGANISM: Streptococcus uberis

<400> SEQUENCE: 2

Met Arg Lys Phe Tyr Tyr Lys Glu Lys Met Glu Ile Lys Gln Lys
1               5                   10                  15

His Gly Lys His Ala Leu Arg Lys Ala Val Thr Ala Ala Val Leu Ala
            20                  25                  30

Gly Thr Ala Phe Ser Ser Leu Gly Gly Phe Ala Gly Ala Val Thr Thr
        35                  40                  45

Val Lys Ala Glu Asp Leu Phe Thr Ile Asn Asn Ser Glu Val Gln Asp
    50                  55                  60

Lys Leu Glu Ser Lys Val Lys Gln Leu Leu Ala Gln Arg Lys Gly
65                  70                  75                  80

Glu Asp Ile Ser Glu Lys Leu Arg Glu Leu Leu Ser Glu Leu Pro Thr
                85                  90                  95
```

```
Asp Ile Leu Lys Asp Ile Met Leu Ser Asn Ile Glu Ala Asp Tyr Leu
            100                 105                 110

Leu Gly Phe Leu Lys Pro Ala Val Glu Glu Met Val Arg Arg Ser Glu
            115                 120                 125

Gln Asn Asp Glu Arg Trp Lys Asp Ile Thr Glu Lys Thr Leu Ala Leu
130                 135                 140

Glu Ala Leu Lys Asp Ser Glu Arg Glu Ile Arg Lys Glu Lys Glu Lys
145                 150                 155                 160

Leu Glu Asp Glu Val Gln Leu Ala Lys Val Lys Ile Glu Thr Lys Glu
                165                 170                 175

Ser Glu Leu Asn Asp Leu Lys Lys Asp Tyr Ile Asp Thr Arg Glu Glu
            180                 185                 190

Leu Ala Asp Thr Ile Glu Glu Leu Asp Glu Val Lys Asn Ser Ile Val
            195                 200                 205

Glu Lys Glu Ala Lys Val Lys Gly Leu Glu Glu Lys Leu Arg Asp Leu
210                 215                 220

Glu Lys Glu Leu Gly Asp Tyr Asp Lys Lys Leu Ser Glu Ala Ala Lys
225                 230                 235                 240

Gln Asn Ser Asp Leu Ser Asn Glu Asn Lys Glu Leu Lys Glu Asn Leu
                245                 250                 255

Asp Thr Ala Glu Asn Ile Thr Val Glu Leu Gln Lys Lys Ser His Glu
            260                 265                 270

Leu Glu Lys Thr Lys Lys Glu Val Glu Leu Glu Leu Lys Ala Glu Lys
            275                 280                 285

Glu Ala Leu Glu Ala Glu Lys Val Lys Leu Ala Glu Ala Asn Glu Ala
290                 295                 300

Asn Asp Lys Leu Ser Glu Glu Arg Asp Ala Ala Lys Glu Lys Glu Ala Glu
305                 310                 315                 320

Lys Val Pro Glu Leu Glu Gly Gln Val Glu Lys Leu Val Glu Glu Ile
                325                 330                 335

Thr Ala Ala Lys Lys Glu Ala Glu Glu Leu Gln Ala Lys Ala Glu Gly
            340                 345                 350

Leu Glu Lys Asp Phe Glu Ala Val Lys Ala Glu Lys Glu Ala Leu Glu
            355                 360                 365

Ala Glu Ile Ala Lys Leu Lys Glu Asp His Gln Lys Glu Val Asp Ala
370                 375                 380

Leu Asn Ala Leu Leu Ala Asp Lys Glu Lys Met Leu Lys Ser Leu Gln
385                 390                 395                 400

Glu Gln Leu Asp Lys Ala Lys Glu Glu Ala Met Lys Asn Glu Gln Met
                405                 410                 415

Ser Gln Glu Glu Lys Ala Lys Leu Gln Ala Glu Leu Asp Lys Ala Lys
            420                 425                 430

Gln Glu Leu Ala Glu Lys Ile Lys Asp Met Pro Asn Lys Val Ala Pro
            435                 440                 445

Gln Ala Glu Gly Lys Ala Asn Ala Gly Gln Ala Ala Pro Asn Gln Asn
450                 455                 460

Gln Asn Asn Gln Ala Gln Ala Asn Gln Ala Lys Asn Ala Asn Asn Leu
465                 470                 475                 480

Pro Ser Thr Gly Asp Lys Pro Val Asn Pro Leu Leu Val Ala Ser Gly
                485                 490                 495

Leu Ser Leu Met Ile Gly Ala Gly Ala Phe Val Tyr Ala Gly Lys Arg
            500                 505                 510

Lys Lys Gly
            515
```

```
<210> SEQ ID NO 3
<211> LENGTH: 1269
<212> TYPE: PRT
<213> ORGANISM: Streptococcus uberis

<400> SEQUENCE: 3

Met Lys Gln Glu Lys Lys Cys Val Asn Trp Phe Met Arg Lys Arg Gly
1               5                   10                  15

Lys Gln Trp Ile Tyr Gly Cys Gly Ile Leu Ile Cys Gly Leu Val Phe
            20                  25                  30

Gly Val Glu Ala Thr Ser Val Ala Ala Glu Thr Ile Pro Thr Thr Ala
        35                  40                  45

Thr Val Glu Thr Leu Asn Ser Asp Val Thr Ser Lys Thr Ser Gln Glu
    50                  55                  60

Thr Gln Lys Thr Thr Glu Ile Ala Thr Pro Val Ser Glu Ile Val Met
65                  70                  75                  80

Pro Ser Gln Gln Lys Val Val Glu Glu Val Thr Gln Glu Val Ser Val
                85                  90                  95

Gln Asn Gln Glu Thr Val Ile Asn Met Pro Val Leu Thr Gln Gly Val
            100                 105                 110

Asn Ile Ala Gly Pro Asn Glu Thr Ala Ile Leu Thr Asp Ser Ile Val
        115                 120                 125

Gln Asn Asn Val Gln Pro Ile Asp Arg Val Glu Lys Met Glu Thr Ser
130                 135                 140

Phe Ser Thr Glu Leu Thr Lys Lys Ala Glu Ser Ser Tyr Asn Thr Asn
145                 150                 155                 160

Leu Gln Asp Leu Asn Tyr Asp Pro Asn Val Trp Glu Val Arg Glu Asp
                165                 170                 175

Gly Leu Tyr Ser Asn Ala Val Gly Lys Gly Asp Asn Phe Leu Phe Ser
            180                 185                 190

Ala Ser Thr Gly Glu Asn Phe Ile Phe Gln Thr Asp Val Thr Phe Leu
        195                 200                 205

Gln Asn Thr Gly Ala Ala Ser Leu Val Phe Arg Ser Asn Asn Asp Pro
    210                 215                 220

Glu Asn Leu Asn Gly Tyr Val Val Asn Leu Asp Gly Asn Ser His Lys
225                 230                 235                 240

Ala Arg Leu Trp Arg Trp Ala Glu Ala Asn Leu Ile Asn Asp Lys Glu
                245                 250                 255

Ile Leu Ala Ser Pro Asp Asn Lys Tyr Phe Leu Lys Val Val Ala Thr
            260                 265                 270

Asn Gly Trp Ile Ser Tyr Tyr Ile Asn Gly Ile Leu Ile Ala Asn Leu
        275                 280                 285

Ser Asp Tyr Thr Ile Gln Arg Asp Asp Leu Gly Gln Thr Thr Tyr Ile
    290                 295                 300

Lys Asp Gly His Phe Gly Leu Leu Asn Trp Asn Gly Glu Met Val Phe
305                 310                 315                 320

Gln Asn Thr Phe Tyr Arg Glu Leu Thr Asn Glu Glu Leu Pro Leu Leu
                325                 330                 335

Asn Asp Val Thr Val Thr Ser Lys Asn Gly Pro Val Gly Pro Lys Gly
            340                 345                 350

Gln Phe Phe Ser Glu Ser Ser Val Tyr Ile Gln Tyr Val Ser Asn Asp
        355                 360                 365

Ala Ser Thr Val Asp Leu Ser Phe Asp Ala Asn Asn Ser Asp Ala Leu
    370                 375                 380
```

```
Ile Thr Val Thr Asp Ala His Gly Lys Val Tyr Ser Asn Pro Ser Ala
385                 390                 395                 400

Ile Pro Val Thr Val Gly Pro Asn Tyr Leu Thr Val Thr Ser Thr Tyr
                405                 410                 415

Thr Thr Thr Asp Gly Tyr Val Ile Pro Ser Thr Tyr Arg Ile Asn Val
            420                 425                 430

His Arg Arg Gln Pro Gln Ser Val Tyr Tyr Asn Glu Asn Phe Arg Asp
        435                 440                 445

Gln Tyr His Tyr Ser Val Lys Asp Gly Trp Ala Asn Asp Pro Asn Gly
    450                 455                 460

Leu Val Tyr Tyr Asn Gly Val Tyr His Met Phe Tyr Gln Phe Tyr Asp
465                 470                 475                 480

Asp Thr Lys Trp Gly Pro Met His Trp Ala His Ala Thr Ser Thr Asp
                485                 490                 495

Leu Ile His Trp Glu Asp Gln Pro Ile Ala Phe Tyr Pro Asp Tyr Asn
            500                 505                 510

Gly Thr Met Phe Ser Gly Cys Ile Val Ala Asp Val Asn Asn Ser Ser
        515                 520                 525

Gly Leu Phe Asp Ser Glu Asn Gly Gly Leu Val Ala Leu Ile Thr Ile
    530                 535                 540

Asn Gly Glu Gly Gln Arg Ile Lys Leu Ala Tyr Ser Thr Asp Glu Gly
545                 550                 555                 560

Lys Thr Trp Gln Lys Val Asp Glu Ile Val Ala Asp Trp Thr Thr Asp
                565                 570                 575

Pro Leu Gln Thr Arg Asp Phe Arg Asp Pro Lys Val Phe Arg Trp Glu
            580                 585                 590

Asn Lys Trp Phe Met Val Ile Ala Gly Gly Pro Leu Arg Leu Tyr Ser
        595                 600                 605

Ser Asp Asp Leu Lys Asn Trp Thr Val Glu Ser Thr Tyr Pro Asp Leu
    610                 615                 620

His Thr Glu Cys Pro Asp Leu Tyr Pro Val Leu Ala Glu Asp Gln Thr
625                 630                 635                 640

Val Lys Trp Val Leu Ser Arg Gly Gly Arg Tyr Tyr Lys Val Gly Asp
                645                 650                 655

Leu Gln Gln Ala Asp Gly Asn Trp Lys Phe Ile Pro Asp Ala Asn Tyr
            660                 665                 670

Gln Glu Thr Asp Ser Ile Met Asn Phe Gly Lys Asp Ser Tyr Ala Ala
        675                 680                 685

Met Thr Tyr Tyr Val Gln Asp Phe Gly Thr Lys Ala Asn Pro Thr Ile
    690                 695                 700

Pro Lys Ile Ile Glu Leu Asn Trp Met Asn Thr Trp Asp Asn Tyr Cys
705                 710                 715                 720

Asn Leu Val Ala Asp Arg Leu Gly Gln Ser Phe Asn Gly Thr Phe Asn
                725                 730                 735

Leu Asn Leu Glu Leu Gly Leu Val Lys Glu Gly Asp Lys Tyr Val Leu
            740                 745                 750

Thr Gln Thr Pro Val Glu Ala Tyr Glu Ser Leu Arg Asp Asn Asp Asn
        755                 760                 765

Lys Val Glu Tyr Lys Asn Val Val Gly Lys Glu Asn Asp Leu Phe
    770                 775                 780

Lys Asp Phe Ser Gly Asp Thr Tyr Glu Ile Val Ala His Phe Lys Pro
785                 790                 795                 800

Ser Asp Lys Thr Thr Lys Val Gly Phe Asn Leu Arg Val Gly Ser Gly
                805                 810                 815
```

-continued

```
Glu Met Thr Lys Val Tyr Tyr Asp Leu Ile Ala Gly Arg Ile Ile Ile
820                 825                 830

Asp Arg Ser Gln Ser Gly Ile Ile Leu Thr Glu Leu Phe Ser Asn Ile
        835                 840                 845

Asp Ser Gln Ala Val Thr Pro Asn Ile Asp Gly Ser Ile Asp Leu His
850                 855                 860

Ile Phe Val Asp Arg Ala Ser Val Glu Val Phe Ser Lys Asn His Thr
865                 870                 875                 880

Val Ala Gly Ala Asn Gln Ile Phe Thr Ser Ala Gln Ser Leu Gly Leu
                885                 890                 895

Glu Val Leu Ile Asp Gly Glu Asp Ala Lys Ala Asp Ile Val Leu Tyr
900                 905                 910

Pro Leu Lys Ser Ile Trp Lys Asn Lys Ile Ile Asp Thr Thr Pro Gln
        915                 920                 925

Ile Val Ile Pro Ala Ser Glu Pro Lys Val Arg Met Asn Val Gly Asp
930                 935                 940

Ser Thr Thr Val Lys Ala Tyr Val Ser Pro Val Gly Ala Ser Gln Asp
945                 950                 955                 960

Leu Ile Trp Asn Ile Ser Asn Pro Ser Leu Val Leu Asp Gln Ile Ser
                965                 970                 975

Gly Asn Gln Val Phe Leu Lys Ala Ile Lys Lys Gly Gln Val Ile Val
            980                 985                 990

Arg Ala Gln Ser Gln Ser Asn Pro Ala Val Tyr Gln Asp Phe Ile Ile
        995                 1000                1005

Asp Ile Leu Glu Asp Asn Phe Asn Thr Asn Val Lys Asp Val Asn
    1010                1015                1020

Val Phe Ser Gly Asp Trp Tyr Val Asp Gly Glu Ser Leu Lys Val
    1025                1030                1035

Ala Asn His Asn Ser Asn Asp Ile Tyr Met Ser Ala Asp Lys Ile
    1040                1045                1050

Pro Tyr Glu Asn Tyr Gln Met Asp Leu Asp Ile Lys Tyr Gly Arg
    1055                1060                1065

Gly Ile Val Asn Ile Phe Phe Ala Ser Gly Asn Pro Asp Ala Asn
    1070                1075                1080

Asn Ala Tyr Thr Ile Gln Phe Gly Ser Asn Asn Ser Val Arg Leu
    1085                1090                1095

Phe Arg Phe Tyr Arg Asp Thr Ile Phe Glu Ala Pro Met Ile Asp
    1100                1105                1110

Val Ile Asn Asp Asn Gln Phe His His Val Arg Leu Val Lys Ser
    1115                1120                1125

Ala Asn Val Ile His Val Tyr Val Asp Asn Glu Met Val Met Ser
    1130                1135                1140

Tyr Thr Phe Asp Gln Val Glu Glu Phe Phe Asn Asn Pro Tyr Leu
    1145                1150                1155

Gly Leu Gly Leu Trp Asp Gly Glu Leu Ala Val Gln Asn Phe Tyr
    1160                1165                1170

Val Ile Asp Leu Asp Ala Gln Lys Pro Val Phe Val Glu Glu His
    1175                1180                1185

Glu Lys Glu Lys Leu Leu Ser Glu Leu Lys Lys Ser Val Val Lys
    1190                1195                1200

Thr Ser Ser Tyr Ser Thr Leu Lys Thr Ile Glu Thr Ser Ser Lys
    1205                1210                1215

Thr Asn Ser Glu Asn Leu Glu Ala Pro Thr Val Ser Lys Lys Asn
    1220                1225                1230
```

```
Leu Pro Met Thr Ser Asp Ser Asn Asn Asn Leu Glu Glu Leu Gly
    1235            1240                1245

Ile Leu Val Ile Leu Thr Thr Leu Gly Ala Phe Leu Gly Arg Val
    1250            1255                1260

Ile Leu Lys Lys Glu Lys
    1265
```

<210> SEQ ID NO 4
<211> LENGTH: 369
<212> TYPE: PRT
<213> ORGANISM: Streptococcus uberis

<400> SEQUENCE: 4

```
Met Lys Lys Lys Gln Glu Met Lys Tyr Tyr Leu Arg Lys Ser Ala Tyr
1               5                   10                  15

Gly Leu Ala Ala Val Ser Val Ala Val Leu Ala Val Gly Ser Pro Val
            20                  25                  30

Ser Ala Gln Glu Lys Ala Ala Ser Thr Glu Ala Thr Pro Lys Val Ala
        35                  40                  45

Pro Lys Val Pro Glu Lys Pro Ser Lys Glu Val Ile Lys Lys Ala Leu
    50                  55                  60

Lys Lys Thr Asp Glu Glu Thr Lys Glu Lys Glu Lys Glu Ala Lys Glu
65                  70                  75                  80

Lys Val Glu Asn Ser Glu Ser Thr Ala Met Val Ser Glu Leu Ser
                85                  90                  95

Ser Thr Asn Glu Glu Thr Ser Ser Glu Glu Asn Asn Thr Asp Glu
            100                 105                 110

Glu Glu Thr Asp Gly Leu Glu Ser Glu Ser Glu Glu Thr Glu Ser
        115                 120                 125

Glu Val Lys Glu Glu Ser Glu Glu Lys Glu Asp Asp Pro Ser Glu
    130                 135                 140

Ser Asp Thr Glu Val Glu Asn Val Glu Ala Ile Asn Leu Ser Glu Ala
145                 150                 155                 160

Glu Gly Asn Asp Ser Ser Lys Pro Glu Thr Ser Glu Glu Val Thr Ala
                165                 170                 175

Glu Glu Asp Arg Gln Glu Thr Asp Arg Leu Ala Glu Val Lys Thr Glu
            180                 185                 190

Glu Ser Ala Lys Glu Gly Asp Glu Asp Ala Asp Lys Lys Asp Glu Ala
        195                 200                 205

Glu Glu Lys Ala Lys Lys Gly Ala Glu Leu Ser Arg Val Lys Ala Glu
    210                 215                 220

Ala Leu Ala Lys Leu Glu Ala Leu Asn Ala Ser Arg Leu Met Lys Lys
225                 230                 235                 240

Ile Val Glu Ser Gly Lys Thr Val Glu Gly Ile Leu Ser Phe Met Lys
                245                 250                 255

Glu Ser Leu Pro Gln Leu Glu Ala Ala Arg Ala Ser Glu Gln Ala Lys
            260                 265                 270

Ala Pro Glu Val Thr Gln Ser Pro Asp His Leu Pro Ser Glu Lys Lys
        275                 280                 285

Ala Val His Asn Pro Val Gln Val Ala Lys Arg Ser Glu Ser Leu Glu
    290                 295                 300

Gln Lys Ala Glu Asn Ala Lys Thr Ser Thr Asn Leu Gln Asn Thr Gln
305                 310                 315                 320

Ile Pro Val Gln Glu Ala Lys Arg Thr Gln Ala Gln Leu Pro Ser Thr
                325                 330                 335
```

```
Gly Glu Asp Tyr Gln Ala Tyr Leu Val Ala Ala Met Ala Leu Ile
                340                 345                 350

Ala Ser Ser Gly Met Val Ala Tyr Gly Ser Tyr Arg Lys Lys Gln
        355                 360                 365

Lys

<210> SEQ ID NO 5
<211> LENGTH: 278
<212> TYPE: PRT
<213> ORGANISM: Streptococcus uberis

<400> SEQUENCE: 5

Met Ser Lys Pro Met Thr Lys Lys Lys Ala Ile Ser Ile Gln Lys
1               5                   10                  15

Ser Val Lys Pro Ile Leu Gly Phe Thr Phe Gly Ala Leu Leu Ser
                20                  25                  30

Thr Val Phe Thr Pro Ser Val Phe Ala Glu Glu Val Val Ser Ser Leu
                35                  40                  45

Gly His Ala Thr Ser Gly Leu Leu Ser Val Ser Val Pro Lys Glu Leu
        50                  55                  60

Thr Ser Leu Glu Thr Thr Thr Tyr Leu Met Ala Ser Glu Ser Pro Ser
65                  70                  75                  80

Asn Thr Leu Thr Ser Asp Thr Ile Ser Ser Asp Asn Gly Gly Thr Ala
                85                  90                  95

Ser Asn Pro Asn Glu Ile Val Thr Thr Glu Thr Thr Ser Glu Ala Ile
                100                 105                 110

Pro Phe Asp Thr Glu Val Ile Gln Asn Pro Asp Leu Pro Ile Gly Glu
        115                 120                 125

Ile Lys Val Val Gln Glu Gly Val Ala Gly Glu Val Thr Val Thr Lys
        130                 135                 140

Thr Thr Thr Thr Ile Thr Leu Asn Gly Val Ser Gln Ser Thr Thr Thr
145                 150                 155                 160

Glu Ser Arg Val Pro Val Lys Lys Pro Ile Asn Lys Ile Ile Glu Val
                165                 170                 175

Gly Thr Lys Glu Ile Ser Thr Ser Pro Ser Ser Ser Asp Val Ile Thr
        180                 185                 190

Val Ser Pro Ser Pro Ser Ser Thr Ser Ser Glu Ser Asn Gln Gln Gly
        195                 200                 205

Ser Leu Thr Pro Ala Pro Lys Ser Arg Gln Asn Ser Gln Glu Lys Lys
210                 215                 220

Gly Ser Gln Thr Lys Lys Ser Lys Asp Asp Ala Lys Glu Lys Glu Gly
225                 230                 235                 240

Asp Lys Lys Glu Leu Pro Pro Thr Gly Ser Gln Glu Ser Gly Ile Phe
                245                 250                 255

Ser Leu Phe Ser Ala Leu Ile Ser Thr Ala Leu Gly Leu Phe Leu Leu
        260                 265                 270

Lys Ser Asn Lys Asn Asp
        275

<210> SEQ ID NO 6
<211> LENGTH: 499
<212> TYPE: PRT
<213> ORGANISM: Streptococcus uberis
```

-continued

<400> SEQUENCE: 6

Met Lys Ser Tyr Leu Lys Arg Arg Tyr Gly Leu Ile Thr Thr Ser Val
1               5                   10                  15

Leu Ala Ala Thr Val Leu Ala Thr Gly Trp Gln Ser Thr Ser Val Leu
            20                  25                  30

Ala Glu Asn Pro Thr Thr Ser Pro Thr Thr Val Thr Ser Asn Gly
        35                  40                  45

Phe Asn Phe Asn Ala Thr Leu Leu Asp His Asn Gly Lys Thr Val Ser
    50                  55                  60

Gly Lys Thr Val Ser Leu Tyr Asp Ile Thr Asp Gly Asn Arg Thr Leu
65                  70                  75                  80

Val Gln Ser Ala Val Ser Asp Gln Asn Gly Ile Ala Ser Phe Ser Gln
                85                  90                  95

Leu Pro Leu Asn Arg Asn Leu Ser Val Phe Val Asp Asn Val Ala Gln
            100                 105                 110

Gly Tyr Thr Thr Arg Thr Ser Glu Ser Gly Gln Val Arg Ser Ser Ala
        115                 120                 125

Phe Tyr Ile Asp Gly Gln Gly Thr Asn Thr Pro Lys Tyr Ser Asp Lys
    130                 135                 140

Thr Ile Thr Ile Ser Val Leu Asn Glu Glu Ala Glu Pro Leu Ala Asn
145                 150                 155                 160

Gln Lys Val Thr Leu Thr Asn Pro Leu Lys Glu Val Val Gly Glu Ala
                165                 170                 175

Met Thr Asp Ala Asp Gly His Val Val Phe Lys Asp Lys Leu Leu Glu
            180                 185                 190

Gly Val Phe Tyr Asn Tyr Ala Val Asn Gly Lys Ala Ile Asp Ser Ala
        195                 200                 205

Gln Pro Asp Ser Lys Arg Ser Val Phe Leu Glu Ser Asn Gln Leu Ala
    210                 215                 220

Lys Glu Gly Phe Thr Phe Thr Ala Thr Ile Leu Gly Lys Asn Gly Lys
225                 230                 235                 240

Thr Val Ala Gly Lys Thr Val Ser Leu Tyr Asp Ile Thr Asp Gly Asn
                245                 250                 255

Arg Thr Leu Val Gln Ser Ala Val Ser Asp Gln Asn Gly Ile Ala Ser
            260                 265                 270

Phe Ser Gln Leu Pro Leu Asn Arg Asn Leu Ser Val Phe Ile Asp Asp
        275                 280                 285

Val Ala Gln Gly Tyr Thr Thr Arg Thr Ser Glu Asn Gly Gln Val Arg
    290                 295                 300

Ser Ser Ala Phe Tyr Val Asp Gly Gln Gly Thr Asn Thr Pro Lys Tyr
305                 310                 315                 320

Ser Asp Lys Thr Ile Thr Ile Ser Val Leu Asn Glu Glu Gly Glu Pro
                325                 330                 335

Leu Ala Asn Gln Lys Val Thr Leu Ile Asn Pro Leu Lys Glu Val Ile
            340                 345                 350

Gly Glu Ala Asn Thr Asp Ala Asn Gly Lys Val Ile Phe Thr Asp Lys
        355                 360                 365

Leu Leu Asp Gly Val Phe Tyr Thr Tyr Ala Val Asn Asp Gln Thr Ile
    370                 375                 380

Asp Ala Thr Gln Pro Asp Thr Ser Arg Asn Val Phe Leu Arg Ala Asp
385                 390                 395                 400

Gln Ile Leu Lys Glu Ser Pro Lys Asn Thr Ala Ser Glu Ala Ala Thr
                405                 410                 415

-continued

```
Asn Leu Glu Lys Thr Thr Glu Ser Lys Glu Gly Asn Met Pro Gln Gln
            420                 425                 430

Asn Gln Ser Glu Ala Lys Glu Lys Ala Pro Glu Lys Gln Val Asp Ala
        435                 440                 445

Asn Ala Ala Asn Lys Lys Ala Pro Gly His Gly Glu Ala Lys Lys Gly
450                 455                 460

Leu Pro Met Ala Gly Glu Arg Gly Ser Arg Leu Phe Thr Phe Ile Gly
465                 470                 475                 480

Leu Ser Leu Ile Leu Gly Ile Ala Gly Tyr Leu Leu Lys His Lys Lys
                485                 490                 495

Val Lys Ser

<210> SEQ ID NO 7
<211> LENGTH: 1144
<212> TYPE: PRT
<213> ORGANISM: Streptococcus uberis

<400> SEQUENCE: 7

Met Val Lys Asn Asn Ile His Ser Arg Lys Lys His Ile Leu Lys Ile
1               5                   10                  15

Ser Leu Leu Ala Thr Ser Val Leu Thr Thr Val Ser Thr Val Ser
            20                  25                  30

Ala Glu Gln Leu Gln Asn Glu Lys Gln Ser Asp Leu Leu Ser Lys Met
        35                  40                  45

Thr Glu Thr Ser Thr Pro His Thr Ile Ile Ser Ser Glu Asp Leu Ser
    50                  55                  60

Asn Ser Asn Gln Glu Ala Asn Gln Lys Asp Glu Thr Ala Ser Lys Ser
65                  70                  75                  80

Leu Gln Pro Met Ile Glu Lys Val Asp Pro Ser His Ile Gln Ala Leu
                85                  90                  95

Trp Glu Lys Val Gly Thr Gly Glu Gly Asp Val Leu Ala Val Ile Asp
            100                 105                 110

Ser Gly Ile Glu Thr Lys His Ser Met Leu Gln Leu Pro Glu Asp Ala
        115                 120                 125

Asp Lys Met Tyr Thr Asp Gln Ala Ser Ile Asp Ser Lys Lys Gln Leu
    130                 135                 140

Leu Gly Ile Glu Arg Gly Gln Trp Ile Asn Asp Lys Leu Pro Phe Tyr
145                 150                 155                 160

His Asp Tyr Thr Gln Gly Glu Glu Ser Ile Asp Arg Asn Thr Tyr His
                165                 170                 175

Gly Thr His Val Ala Gly Ile Ala Thr Ala Ser Gly Leu Thr Gln Lys
            180                 185                 190

Glu Asn Lys Glu Gln Met Gln Gly Ile Val Pro Asn Ala Gln Leu Leu
        195                 200                 205

Phe Leu Lys Val Gly Gln Pro Ser Val Glu Gly Glu Arg Glu Lys His
    210                 215                 220

Tyr Ala Met Ala Ile Lys Asp Ala Ile Ala Leu Gly Ala Thr Ala Ile
225                 230                 235                 240

Asn Met Ser Phe Gly Gln Val Gly Lys Ala Ser His Glu Leu Asn Asp
                245                 250                 255

Asp Phe Lys Lys Ala Leu Ala Leu Ala Ala Asp Lys Gly Val Ala Ile
            260                 265                 270

Val Val Ala Ala Gly Asn Asp Tyr Ala Met Gly Gly Ser Gln Thr Lys
        275                 280                 285
```

```
Pro Leu Ala Lys Asn Pro Asp Thr Gly Val Ile Gly Thr Pro Ala Thr
            290                 295                 300

Thr Glu Glu Val Phe Thr Val Ala Ala Tyr Val Ala Pro His Tyr Trp
305                 310                 315                 320

Ser Arg Val Leu Ser Val Thr Asp Gly Ser Thr Ser Lys Ala Leu Ala
                325                 330                 335

Leu Glu Met Ala Ser Pro Phe Ala Glu Asn Lys Asp Tyr Glu Leu Ile
            340                 345                 350

Phe Leu Glu Lys Gly Leu Glu Thr Glu Glu Asn Ala Glu Arg Leu Lys
        355                 360                 365

Asn Lys Val Leu Val Leu Asn Tyr Asp Phe Val Thr Asn Ser Lys Glu
    370                 375                 380

Val Ala Glu Lys Val Glu Ala Leu Gly Ala Ala Gly Val Leu Val His
385                 390                 395                 400

Asn Asn Gln Ala Lys Lys Pro Leu Ile Pro Leu Ala Tyr Asn Gly Pro
                405                 410                 415

Leu Pro Met Gly Phe Ile Ser Lys Glu Asp Ala Asp Trp Leu Lys Thr
            420                 425                 430

Met Thr Ser Pro Gln Phe Arg Leu Lys Lys Glu Lys Gln Leu Val Glu
        435                 440                 445

Val Pro Gly Gly Arg Gln Met Thr Asn Phe Ser Ser Trp Gly Leu Ser
    450                 455                 460

Val Asp Gly Asn Met Lys Pro Asp Phe Ala Ala Pro Gly Tyr Glu Ile
465                 470                 475                 480

Tyr Ser Pro Thr Pro Gly Asn Asp Tyr Ser Lys Met Ser Gly Thr Ser
                485                 490                 495

Ala Ala Ser Pro His Ala Met Gly Ile Ile His Leu Val Arg Lys His
            500                 505                 510

Ile Gln Lys Glu Tyr Pro His Leu Ser Ala Lys Glu Gln Leu Gln Leu
        515                 520                 525

Val Lys Asn Leu Leu Met Ser Thr Ala Ser Pro Ile Tyr Ser Glu Leu
    530                 535                 540

Asp His Ser Tyr Tyr Ser Pro Arg Val Gln Gly Ala Gly Ala Leu Asp
545                 550                 555                 560

Ala Lys Lys Ala Leu Glu Thr Asp Val Tyr Val Thr Ala Ala Asp Gly
                565                 570                 575

Leu Ser Lys Ile Gln Leu Gly Asp Val Asn Asn Gln Phe Glu Leu Arg
            580                 585                 590

Val Thr Leu His Asn Leu Ser Asn Gln Glu Lys Asn Phe Thr Tyr Phe
        595                 600                 605

Ala Arg Val Leu Thr Asp Lys Val Glu Lys Gly Arg Ile Leu Leu Arg
    610                 615                 620

Pro Gln Glu Leu Tyr Gln Thr Arg Pro Leu Gln Val Lys Leu Ala Pro
625                 630                 635                 640

Asn Gln Lys Gln Glu Val Val Ile Lys Val Asp Ile Ser Asn Phe Asp
                645                 650                 655

Gln Gln Leu Lys Ala Gln Met Pro Asn Gly Tyr Phe Leu Asp Gly Phe
            660                 665                 670

Val Val Phe Gln Ser Lys Glu Gly Ala Gln Lys Asp Leu Ser Ile Pro
        675                 680                 685

Phe Ile Ala Phe Lys Gly Lys Phe Ala Asp Leu Glu Ala Leu Asp Ser
    690                 695                 700

Pro Ile Tyr Arg Asn Leu Asp Gly Thr Phe Tyr Tyr Ser Pro Lys Glu
705                 710                 715                 720
```

-continued

```
Gly Gln Asp Pro Tyr Asp Phe Glu Val Asp Ser Ile Gln Gln Ile Lys
                725                 730                 735
Glu Gln Tyr Met Thr Gly Leu Ile Thr Thr Phe Thr Pro Trp Ser Leu
            740                 745                 750
Val Glu Gly Ser Lys Ile Asp Gly Phe Ser Pro Glu Met Ala Ser Glu
        755                 760                 765
Phe Ser Thr Thr Asp Tyr Leu Gly Ser Tyr Asn Lys Glu Gly Asp Asn
    770                 775                 780
Thr Val Arg Arg Phe Arg Phe Val Glu Gly Lys Pro Tyr Leu Ala Leu
785                 790                 795                 800
Ser Pro Asn Gly Asp Asp Asn Met Asp Lys Val Gly Phe Arg Gly Val
                805                 810                 815
Phe Leu Arg Asn Val Arg Asp Ile Lys Ala Gln Val Phe Ala Ser Asp
            820                 825                 830
Asp Leu Gln His Pro Ile Trp Glu Ser Pro Ile Lys Ala Phe Ala Lys
        835                 840                 845
Lys Asp Val Asn Thr Asn Asp Ile Lys Glu Ser Met Leu Glu Asn Thr
    850                 855                 860
Val Trp Glu Gly Lys Asp Ala Ser Gly Asn Pro Val Thr Glu Gly Leu
865                 870                 875                 880
Tyr Arg Tyr Arg Val Thr Tyr Thr Pro Leu Ala Glu Gly Ala Lys Glu
                885                 890                 895
Gln Phe Ile Asp Phe Asp Ile Leu Val Asp Leu Thr Pro Ser Lys Leu
            900                 905                 910
Pro Gln Ser Ala Ile Leu Met Leu Ala Glu Arg Arg Ile Glu Leu Thr
        915                 920                 925
Glu Ser Arg Asp Tyr Leu Ser His Asp Thr Tyr Arg Asp Arg Leu Tyr
    930                 935                 940
Tyr Lys Tyr Gly Thr Asp Asp Ile Asn Phe Thr Thr Phe Glu Lys Asp
945                 950                 955                 960
Asp Met Gly His Phe Val Ile Pro Asn Gln Val Glu Asp Gly Leu Ser
                965                 970                 975
Gly Glu Lys Ile Thr Ile Asn Leu Asp Lys Thr Asp His Phe Phe Phe
            980                 985                 990
Val Arg Glu Asp Phe Ser Gly Asn  Phe Ser Val Ile Ser  Leu Ser Gln
        995                 1000                 1005
Leu Leu  Asn Asn His Ser Asp  Gln Met His Ser Leu  Glu Glu Ser
    1010                 1015                 1020
Lys Ser  Asp Arg Lys Glu Ser  Asn Thr Gly Asp Ile  Arg His Glu
    1025                 1030                 1035
Lys Gln  Glu Asn Leu Ser Gln  Gln Thr Leu Leu Ser  Thr Pro Ser
    1040                 1045                 1050
Ile Asp  Gly Gln Lys Gln Asn  Asp Gln Leu Met Val  Glu Lys Glu
    1055                 1060                 1065
Lys Asp  Ile Met Asp Glu Ser  Lys Ser Glu Arg Ser  Glu Lys Asn
    1070                 1075                 1080
Lys Phe  Pro Lys Val Pro Ala  Ser Ile Thr Leu Lys  Asp Gly Thr
    1085                 1090                 1095
Leu Tyr  Pro Gln Ser Ile Ser  Gln Lys Thr Ser Leu  Pro Lys Thr
    1100                 1105                 1110
Val Asp  Ser Gln Lys Thr Met  Thr Phe Leu Gly Ile  Ala Met Leu
    1115                 1120                 1125
```

```
Phe Gly Gly Ile Leu Gln Val Leu Trp Ser Tyr Phe Lys Lys Arg
    1130                1135                1140

Asp

<210> SEQ ID NO 8
<211> LENGTH: 484
<212> TYPE: PRT
<213> ORGANISM: Streptococcus uberis

<400> SEQUENCE: 8

Met Thr His Met Asn Asn Gly Arg Tyr Lys Gln Arg Phe Ser Leu
1               5                   10                  15

Arg Lys Tyr Lys Phe Gly Ala Ala Ser Val Leu Leu Gly Thr Ile Phe
            20                  25                  30

Ala Leu Gly Met Thr Gly Thr Thr Ala Gln Ala Gln Met Pro Ser His
                35                  40                  45

Ser His Pro Gly Gly Val Tyr Pro Gly Gly Ile Ile Pro Gly Ala Pro
        50                  55                  60

Gly Ala Ile Pro Gly Ile Pro Gly Gly Ser Gly Phe Asp Phe Asp
65                  70                  75                  80

Pro Ser Gly Tyr Pro Ala Gly Pro His Gly Tyr Leu Pro Ser Tyr Gly
                85                  90                  95

Pro Gly Gly Val Gly Met Leu Gln Gly Pro Gly Pro Ala Gly Pro
            100                 105                 110

Ile Gly Pro Asn Gly Ile Pro Gly Glu Arg Gly Pro Val Gly Pro Ala
                115                 120                 125

Gly Ala Glu Gly Pro Arg Gly Pro Lys Gly Asp Lys Gly Glu Thr Gly
        130                 135                 140

Gln Gln Gly Pro Arg Gly Glu Ala Gly Ile Ala Gly Pro Ser Gly Pro
145                 150                 155                 160

Gln Gly Pro Ala Gly Val Ala Gly Pro Ala Gly Pro Gln Gly Val Ala
                165                 170                 175

Gly Arg Asp Gly Arg Asp Gly Arg Asp Gly Arg Pro Gly Glu Ala Gly
            180                 185                 190

Leu Asp Gly Leu Asp Gly Leu Asn Gly Leu Asn Gly Ile Asp Gly Thr
        195                 200                 205

Asp Gly Lys Asp Gly Lys Asp Gly Lys Asp Gly Gln Asn Gly Gln Asp
    210                 215                 220

Gly Lys Asn Gly Arg Asn Gly Gln Asp Gly Gln Lys Gly Lys Asp Gly
225                 230                 235                 240

Gln Asn Gly Arg Asn Gly Gln Asp Gly Lys Ala Gly Lys Asp Gly Lys
                245                 250                 255

Ser Gly Thr Asp Gly Lys Asn Gly Lys Ala Gly Thr Asp Gly Lys Asn
            260                 265                 270

Gly Lys Ser Gly Lys Asp Gly Lys Ala Gly Thr Asp Gly Lys Asn Gly
        275                 280                 285

Arg Ala Gly Thr Asp Gly Lys Asn Gly Lys Ala Gly Gln Asp Gly Lys
    290                 295                 300

Asp Gly Lys Asn Gly Thr Asp Gly Leu Asn Gly Arg Asp Gly Arg Asp
305                 310                 315                 320

Gly Arg Asp Gly Arg Asp Gly Arg Asp Gly Leu Asp Gly Lys Asp Gly
                325                 330                 335

Lys Asn Gly Lys Asp Gly Glu Ser Pro Ile Ile Asn Val Lys Asp Asn
            340                 345                 350
```

```
Gly Asn Gly Ser His Thr Ile Thr Phe Leu Asn Pro Asp Gly Ser Arg
            355                 360                 365

Lys Glu Val Thr Ile Ser Asn Gly Lys Asp Gly Gln Pro Gly Arg Asp
    370                 375                 380

Gly Lys Asp Gly Arg Asp Gly Lys Asp Gly Met Pro Gly Arg Asp Gly
385                 390                 395                 400

Met Asn Gly Lys Asp Gly Gln Ala Ala Gly Asn Thr Ala Gly Lys
            405                 410                 415

Gly Asn Ala Ser Asp Met Lys Pro Lys Ala Met Ala Ala Pro Ala Ala
            420                 425                 430

Met Thr Asn Gln Asn Ala His Ala Asn Asn Gly Pro Ala Lys Ala
            435                 440                 445

Gln Leu Pro Ser Thr Gly Asp Lys Ala Asn Pro Phe Phe Thr Ala Ala
    450                 455                 460

Ala Leu Ala Val Met Ser Ala Gly Met Val Ala Val Ser Arg Lys
465                 470                 475                 480

Arg Lys Glu Asp

<210> SEQ ID NO 9
<211> LENGTH: 1482
<212> TYPE: PRT
<213> ORGANISM: Streptococcus uberis

<400> SEQUENCE: 9

Leu Arg Tyr Lys Lys Met Thr Arg Ser Ser Asn Ser Arg Ile Val Leu
1               5                   10                  15

Gln Ser Thr Leu Ile Met Ile Phe Ala Ser Ser Cys Val Asn His Phe
            20                  25                  30

Lys Gly Thr Ile His Ala Asp Glu Lys Val Ile Asn Gly Ser Glu Ala
        35                  40                  45

Ser Ile Gln Val Asp Tyr Thr Leu Asn Thr Ala Ser Glu Asn Arg Gln
    50                  55                  60

Ile Pro Glu Glu Lys Val Thr Glu Ala Thr Asn Asp Gln Pro Glu
65                  70                  75                  80

Leu Leu Glu Lys Gln Ala Ala Phe Leu His Glu Gly Arg Glu Lys Asn
                85                  90                  95

Thr Glu Asn Leu Pro Leu Asp Gly Arg Gly Ser Leu Ile Ala Ser Ile
            100                 105                 110

Asp Ser Gly Val Asp Ile Lys His Glu Ala Phe Ala Asn Asn Asp Asp
        115                 120                 125

Asn His Asp Phe His Lys Glu Thr Glu Val Ser Glu Gly Ser Thr Ser
    130                 135                 140

Lys Ile Pro Phe Val Tyr Asp Phe Leu Ser Gly Asp Thr Ser Val Arg
145                 150                 155                 160

Asp Asp Glu Glu Glu His Gly Met His Ile Ala Gly Ile Leu Val Gly
                165                 170                 175

Asp Ser Lys Lys Gly Phe Lys Gly Met Ala Pro Lys Ala Gln Leu Ile
            180                 185                 190

Ala Tyr Arg Thr Trp Ser Lys Asn Asn Ser Glu Gly Tyr Gln Glu Ala
        195                 200                 205

Asn Gln Phe Phe Ala Met Lys Asp Ala Ile Lys Arg Gly Ala Asp Val
    210                 215                 220

Ile Ser Leu Ser Ile Gly Glu Ile Gly Ser Gly Gln Asn Asp Asp Ile
225                 230                 235                 240
```

```
Trp Ala Lys Val Leu Glu Glu Ala Lys Lys Asn Val Val Val
            245                 250                 255

Ala Ala Met Gly Asn Tyr Gly Thr Ser Ala Thr Ser Asn Thr Phe Asp
                260                 265                 270

Gln Val Val Asp Glu Thr Phe Pro Gln Thr Asp Ser Ser Thr Leu Leu
            275                 280                 285

Ser Val Ser Ala Asn Pro Glu Val Ile Gly Val Gly Ser Ile Phe Glu
            290                 295                 300

Lys Glu Met Tyr Leu Pro Thr Leu Lys Ile Asp Thr Leu Glu Val Pro
305                 310                 315                 320

Tyr Glu Asn Ile Asn Trp Gln Asn Tyr Leu Phe Lys Gln Glu Lys
                325                 330                 335

Gln Glu Arg Ile Ser Phe Asn Glu Met Leu Ile Thr Leu Asn Gln Ser
            340                 345                 350

Lys Glu Glu Gly Ser Leu Lys Asp Lys Val Val Ile Glu Arg Gln
                355                 360                 365

Ala Glu Asn Ile Phe Pro Gln Leu Lys Glu Val Met Lys Lys Gly Ala
            370                 375                 380

Lys Gly Val Ile Leu Ile Asn Gln Ser Gly Pro Thr Thr Tyr Gly Asn
385                 390                 395                 400

Tyr Glu Thr Val Pro Glu Leu Arg Asn Thr Leu Leu Asp Asp Glu Asp
                405                 410                 415

Gly Asp Phe Lys Lys Thr Trp Ala Val Ser Ile Ser Ala Asn Asp Gly
            420                 425                 430

Lys Ala Leu Lys Asp Tyr Leu Gln Lys Gln Asp Lys Lys Lys Ser Tyr
            435                 440                 445

Ser Leu Val Phe Asn Thr Lys Pro Gln Leu Lys His Val Phe Lys Tyr
            450                 455                 460

Pro Gly Val Ser Gly Phe Ser Thr Trp Gly Pro Gly Leu Asp Leu Thr
465                 470                 475                 480

Leu Lys Pro Asp Ile Val Ala Pro Gly Glu Asn Ile Tyr Ser Thr Gly
                485                 490                 495

Asn Asp Asn Ser Tyr Phe Ile Ser Ser Gly Thr Ser Met Ser Ala Pro
            500                 505                 510

Lys Val Ala Gly Ala Ser Ala Met Phe Leu Pro Val Thr Lys Lys Trp
            515                 520                 525

Gln Lys Lys Trp Glu Lys Gln Asn Val Ser Met Ser Ile Pro Gln Leu
            530                 535                 540

Thr Lys Leu Leu Phe Gln Asn Thr Ala Asp Ile Leu Tyr Asp His Ser
545                 550                 555                 560

Val Pro Asn Gly Lys Pro Ile Leu Pro Tyr Ser Pro Arg Arg Gln Gly
                565                 570                 575

Ala Gly Ala Leu Asn Val Lys Lys Ala Gln Thr Asn Val Phe Val
            580                 585                 590

Thr Ser Ala Asp Asn Lys Gly Ala Ile Leu Lys Asp Phe Lys Glu
            595                 600                 605

Ser Arg Lys Glu Phe Asp Ile Val Ile Arg Asn Phe Ser Asp Gln Val
            610                 615                 620

Arg Arg Phe Lys Ile Glu Pro Gly Ser Val Leu Gly Lys Ile Leu Tyr
625                 630                 635                 640

Ser Lys Asp Arg Lys Asn Tyr Asp Lys Asn Glu Thr Ile Gln Thr Val
                645                 650                 655

His Ser Arg Val Ile Lys Asp Ser Ala Ile Glu Ser Pro Leu Tyr Val
                660                 665                 670
```

-continued

```
Gln Ile Ala Pro Asn Ser Ser Met Ile Leu Pro Leu Lys Leu Asn Val
        675                 680                 685

Gly Lys Ala Val Glu Asn Glu Phe Val Glu Gly Phe Ile Lys Leu Arg
        690                 695                 700

Ser Leu Glu Lys Asp Gln Pro Asp Leu Asn Ile Pro Met Gly Phe Tyr
705                 710                 715                 720

Gly Asp Trp Asn Ser Glu Asn Ile Leu Asp Pro Val Ala Trp Gln Glu
                725                 730                 735

Gly Ser Lys Thr Arg Leu Thr Gly Ile Val His Pro Tyr Gly Leu Gly
            740                 745                 750

Glu Asp Lys Phe Asp Ile Val Pro Trp Gly Val Asp Tyr Glu Lys Trp
        755                 760                 765

Lys Gln Asp Pro Lys Ala Leu Asp Ala Asp Gln Arg Phe Tyr Val Met
770                 775                 780

Gln Ser Gln Ala Gly Ile Ala Asn His Ala Lys Met Arg Leu Arg Leu
785                 790                 795                 800

Ile Phe Met Arg His Ala Lys Asp Tyr Arg Val Asp Ile Leu Asn Ser
                805                 810                 815

Gln Lys Asp Lys Val Leu Lys Thr Leu Lys Thr Gly His Gln Ala Pro
        820                 825                 830

Lys Tyr Met Glu Ser Ala Leu Leu Glu His Gly Asp Gln Tyr Gln Met
835                 840                 845

Gln Phe Ala Asp Phe Asp Pro Asp Leu Glu Trp Asp Gly Ser Val Tyr
850                 855                 860

Asn Pro Lys Thr Asn Thr Glu Asp Pro Leu Pro Asp Gly Asn Tyr Phe
865                 870                 875                 880

Ile Arg Val Ser Ser Arg Ile Ser Lys Asn Arg Pro Tyr Gln Glu His
                885                 890                 895

Ile Ile Pro Phe Ala Ile Asp Asn Gln Lys Pro Lys Val Lys Ile Glu
            900                 905                 910

Glu Lys Thr Ala Leu Gln Val Val Phe His Val Asp Asp Ala His Leu
        915                 920                 925

Gln Gly Ile Arg Leu Val Lys Asp Asn Lys Ile Ile Gln Thr Leu Glu
        930                 935                 940

Thr Asp Thr Gln Gly Arg Phe Arg Leu Asn Leu Ala Asp Phe Gln Gly
945                 950                 955                 960

Lys Gly Phe Glu Leu Glu Ala Ile Asp Phe Ala Glu Asn Lys Thr Ile
                965                 970                 975

Ile Asp Leu Asp Ser Leu Lys Glu Lys Glu Val Gly Tyr Leu Phe Gly
            980                 985                 990

Ala Ser Ser Ser Tyr Asn Lys Ser Arg Tyr Arg Ser Pro Arg Ser Val
        995                 1000                1005

Ala His Lys Asn Ala Glu Asp Ile Leu His Glu Asn Ser Glu Glu
        1010                1015                1020

Ser Glu Glu Ile Ala Ser Ala Leu Thr Phe Glu Asp Gly Ser Asp
        1025                1030                1035

Phe His Asp Gly Lys Lys Thr Asn Ala Tyr Ser Glu Ile Asn Lys
        1040                1045                1050

Ser Asn Asp Asn Ser Val His Leu Lys Asp Asn Thr Tyr Tyr Arg
        1055                1060                1065

Asp Tyr Tyr Ile His Leu Lys Glu Gly Gln Arg Leu Leu Val Thr
        1070                1075                1080

Thr Thr Asn Ala Phe His Asn Ser Lys Gln Gly Asn Asp Ile Thr
        1085                1090                1095
```

```
Ala Pro Thr Trp Gln Ala Asn Tyr Thr Tyr Asp Pro Ser Thr Asn
    1100            1105                1110
Gln Gly Gln Tyr Tyr Arg Lys Ile Ala Ile Pro Ile Tyr Gln Gly
    1115            1120                1125
Ser Asn Thr Ile Asn Val Lys Ala Phe Tyr Lys Asp Lys Leu Ile
    1130            1135                1140
Phe Asn Lys Gly Tyr Ala Val Lys Leu Asp Thr Glu Val Pro Gln
    1145            1150                1155
Leu Thr Phe Asp Asn Pro Asn Ile Ser Phe Thr Ser Asp Lys Trp
    1160            1165                1170
Gln Asn Leu Ser Asp Asp Glu Tyr Asp Asp Asn Ile Val Gly
    1175            1180                1185
Thr Ile Thr Ile Pro Asn Asn Thr Leu Arg Leu Ser Gly Lys Ile
    1190            1195                1200
Arg Asp Gly Leu Asp Gly Trp Arg Met Phe Ile Asn Gly Asp Met
    1205            1210                1215
Val Asp Ser Asp Ile Lys Leu Gly Glu Tyr Asp Asp Ile Phe Gln
    1220            1225                1230
Gln Asn Arg Arg Gln Trp Lys Tyr Glu Lys Gln Val Glu Asn Asp
    1235            1240                1245
Asp Tyr Val Leu Ile Lys Leu Ser Asp His Val Lys Asn Ser Arg
    1250            1255                1260
Ser Tyr Leu Phe Lys Val Lys Ile Asp Pro Thr Val Ser Glu Tyr
    1265            1270                1275
His Phe Thr Asn Lys Asn Asp Ile Ile Asp Asp Asp Lys Thr Leu
    1280            1285                1290
Leu Thr Leu Asn Thr Leu Thr Asp Ser Ser Leu Gly Tyr Ala Asn
    1295            1300                1305
Lys Leu Leu Asn Met Pro Lys Asp Leu Val Lys Ser Thr Asp Asp
    1310            1315                1320
Leu Phe Lys Ala Met Thr Met Leu Phe Lys Lys Glu Ser Phe Phe
    1325            1330                1335
Leu Tyr Pro Leu Lys Asn Asp Leu Asn Thr Asn Gly Ile Ser Met
    1340            1345                1350
Met Thr Ser Leu Val Gln Phe Gln Ala Lys Asp Val Lys Glu Asn
    1355            1360                1365
Ile Pro Leu Glu Trp Glu Ile Lys Thr Lys Ala Ser Asp Ser Arg
    1370            1375                1380
Gln Leu Leu Tyr Gln Asn Leu Lys Asn Glu Lys Glu Arg Leu Asp
    1385            1390                1395
Gln Val Ser Thr Asn Pro Leu Ala His Gln Leu Pro Leu Glu Asn
    1400            1405                1410
Ser Asn Gln Glu Asn Gly Gln Asp Ala Ile Leu Thr Ser Thr Lys
    1415            1420                1425
Val Leu Pro Met Ser Lys Ser Ser Ile Phe Arg Asp Ser Leu Arg
    1430            1435                1440
Glu Thr Ser Leu Pro Glu Thr Arg Asp Ser Ser Met Ala Asn
    1445            1450                1455
Trp Ser Leu Ala Phe Phe Leu Ser Ala Val Ile Cys Phe Phe Lys
    1460            1465                1470
Gly Arg Arg Lys Arg Leu Asn Lys Leu
    1475            1480
```

```
<210> SEQ ID NO 10
<211> LENGTH: 550
<212> TYPE: PRT
<213> ORGANISM: Streptococcus uberis

<400> SEQUENCE: 10

Met Glu Asn Gln Asn Gln Leu Thr Leu Gln Gly Ile Leu Gly Lys Cys
1               5                   10                  15

Leu Lys Trp Phe Leu Leu Leu Ser Ile Ser Leu Phe Thr Ala Phe Pro
            20                  25                  30

Phe Ile Trp Met Leu Ile Ser Ser Leu Lys Thr Lys Ala Glu Val Met
        35                  40                  45

Asn Thr Glu Val Ile Trp Pro His Ile Pro Gln Trp Gly Asn Tyr Leu
    50                  55                  60

Glu Ile Phe Thr Gln Ser Pro Ile Pro Lys Tyr Ile Trp Asn Ser Leu
65                  70                  75                  80

Trp Thr Ser Val Val Ile Val Leu Ile Gln Ile Val Thr Gly Ala Met
                85                  90                  95

Leu Ala Tyr Ala Leu Val Phe Leu Arg Phe Lys Gly Arg Gln Leu Ile
            100                 105                 110

Phe Ala Ile Val Met Gly Thr Tyr Met Leu Pro Ala Ala Ala Thr Tyr
        115                 120                 125

Ile Pro Ser Tyr Ile Ile Leu Ser Lys Gly Gly Met Leu Asn Thr Leu
    130                 135                 140

Thr Gly Leu Ile Val Ser Ser Thr Ile Ser Ile Phe Gly Ile Phe Leu
145                 150                 155                 160

Leu Arg Gln Ala Phe Met Gln Val Pro Arg Ser Leu Ile Glu Ala Ser
                165                 170                 175

Arg Met Asp Gly Ala Ser His Phe Arg Val Leu Trp Glu Ile Val Cys
            180                 185                 190

Pro Met Thr Lys Ser Ser Phe Ile Thr Phe Gly Leu Met Ser Phe Ile
        195                 200                 205

Ala Ala Tyr Asn Ser Gly Lys Glu Thr Ser Ile Gly Asp Val Thr Leu
    210                 215                 220

Thr Phe Ser Lys Glu Leu Val Pro Val Pro Asn Ile Asp Glu Glu Ile
225                 230                 235                 240

Val Ile Pro Ser Ile Pro Glu Lys Pro Leu Val Glu Pro Glu Val Asp
                245                 250                 255

Ser Ile Leu Pro Leu Ile Pro Leu Gln Pro Ser Leu Pro Ile Tyr Pro
            260                 265                 270

Ser Pro Asp Leu Pro Glu Met Glu Gln Pro Asp Gln Asp Ser Pro Glu
        275                 280                 285

Ile Ser Gly Gln Ser Gln Ile Val Asp Ile Val Glu Asp Thr Leu Pro
    290                 295                 300

Gly Val Ser Gly Gln Gln Ser Ser Ser Glu Glu Thr Glu Ile Thr Glu
305                 310                 315                 320

Asp Thr Arg Pro Glu Ser Asp Asn Glu Ile Ile Ile Gly Gly Gln Ser
                325                 330                 335

Glu Leu Val Asp Ile Val Glu Asp Thr Gln Ser Gly Met Ser Gly Gln
            340                 345                 350

His Ser Ser Ser Glu Glu Thr Glu Ile Ser Glu Asp Thr Arg Pro Glu
        355                 360                 365

Ser Asp Asn Glu Ile Ile Val Gly Gly Gln Asn Glu Leu Val Asp Ile
    370                 375                 380
```

```
Val Glu Asp Thr Gln Pro Ser Leu Ser Gly His Gln Ser Glu Ser Gln
385                 390                 395                 400

Glu Thr Val Thr Val Glu Asp Thr Gln Pro Asn Gln Thr Asn Ile Leu
            405                 410                 415

Ile Gly Gly Gln Ser Glu Ile Val Asp Ile Glu Asp Thr Gln Ala
        420                 425                 430

Gly Met Thr Gly Gln Tyr Ser Ser Thr Asp Gln Leu Thr Ile Val Glu
        435                 440                 445

Asp Thr Leu Pro Glu Gln Met Glu Glu Thr Asp Glu Ile Lys Ser Asp
    450                 455                 460

Ser Gln Val Met Asp Ile Pro Lys Val Asn Asp Thr Asn Asn Asp Lys
465                 470                 475                 480

Gly Ala Lys Ala Ser Val Ala Phe Asp Val Glu Glu Ser Lys Val Val
            485                 490                 495

Thr Thr Gln Asp Ile Lys Pro Ser Thr Tyr Val Lys Gly Asp Asn Gln
        500                 505                 510

Leu Pro Gln Thr Gly Asp Asp Asn Val Asn Ala Phe Phe Thr Leu
    515                 520                 525

Ala Ala Leu Ser Val Ile Gly Ala Thr Gly Leu Arg Gln Asn Lys Arg
530                 535                 540

Arg Glu Lys Glu Arg Asn
545                 550

<210> SEQ ID NO 11
<211> LENGTH: 93
<212> TYPE: PRT
<213> ORGANISM: Streptococcus uberis

<400> SEQUENCE: 11

Val Val Lys Val Thr Val Asp Gly Ser Asp Asn Ser Thr Ile Asp Ser
1               5                   10                  15

Gly Phe Val Lys Val Glu Gln Pro Thr Pro Gly Ser Asn Ser Ser Ser
            20                  25                  30

Glu Ser Leu Ser Gln Ser Thr Thr Gln Ser Ser Ser Gln Ser Ser Ser
        35                  40                  45

Ala Lys Pro Val Ala Ser Gln Thr Ala Ala Glu Leu Pro His Thr Gly
    50                  55                  60

Gln Ala Glu Asn Asn Gly Leu Tyr Gly Ser Ala Ala Leu Ala Ile Leu
65                  70                  75                  80

Ala Ala Leu Gly Leu Ala Gly Lys Lys Arg Asp Glu Lys
                85                  90

<210> SEQ ID NO 12
<211> LENGTH: 1116
<212> TYPE: PRT
<213> ORGANISM: Streptococcus uberis

<400> SEQUENCE: 12

Met Phe Lys Thr Lys Lys Glu Ile Phe Ser Ile Arg Lys Thr Ala Leu
1               5                   10                  15

Gly Val Gly Ser Val Leu Leu Gly Val Ile Leu Thr Thr Gln Val Ala
            20                  25                  30

Ser Ala Asn Glu Val Ser Leu Met Thr Pro Ser Val Asp Lys Ser Leu
        35                  40                  45

Thr Thr Thr Ser Pro Val Leu Glu Ser Thr Ser Ser Gln Leu Ala Ala
    50                  55                  60
```

-continued

```
Thr Thr Ala Pro Thr Thr Asp Thr Thr Ser Asn Val Thr Ala Thr
 65                  70                  75                  80

Ser Pro Val Leu Ala Ala Thr Thr Ala Pro Ser Val Thr Thr Ser
                 85                  90                  95

Pro Ile Ala Ser Pro Ile Arg Tyr Val Ser Asp Pro Asn Gln Pro Val
            100                 105                 110

Gly Tyr Arg Ala Thr Gln Val Gln Gly Thr Asp Gly Ser Ile Ile Thr
            115                 120                 125

Thr Gln Thr Gly Ala Leu Asp Ala Asn Gly Asn Pro Ile Val Thr Val
130                 135                 140

Glu Arg Ile Glu Pro Thr Lys Thr Val Ile Val Leu Gly Thr Lys Ser
145                 150                 155                 160

Thr Ser Gln Val Thr Ser Thr Gln Ala Ala Thr Thr Thr Tyr Ser Ile
                165                 170                 175

Asp Val Thr Lys Pro Val Gly Thr Asp Val Val Ile Pro Ala Val Asp
                180                 185                 190

Gly Gln Thr Thr Thr Thr Thr Thr Tyr Lys Ile Glu Thr Ala Thr Thr
                195                 200                 205

Ala Pro Val Ser Pro Ser Val Leu Ser Glu Gly Tyr Lys Trp Ile Asp
210                 215                 220

Gln Pro Phe Tyr His Val Asp Thr Thr Gln Thr Leu Pro Ser Asp Arg
225                 230                 235                 240

Ile Ser Ile Asp Gln Leu Phe Val Pro Met Pro Val Leu Thr Pro Asp
                245                 250                 255

Tyr Asn Thr Thr Glu Ser Thr Val Arg Glu Tyr Ala Gln Tyr Ala Glu
                260                 265                 270

Asn Tyr Met Tyr Asp Tyr Ile Thr Val Thr Asn Pro Asp Gly Ser Thr
                275                 280                 285

Thr Arg Gln Gln Val Ile Arg Pro Val Thr Ser Glu Met Leu Asp Pro
                290                 295                 300

Thr Asn Thr Arg Leu Arg Thr Leu Thr Gly Leu Thr Asp Asp Asn Ala
305                 310                 315                 320

Phe Tyr Ser Arg Leu Phe Asp Ala Ser Gln Gln Asp Leu Trp Asn Thr
                325                 330                 335

Ser Ala Gln Asp Tyr Gly Leu Glu Ile Val Pro Glu Asp Leu Ser Thr
                340                 345                 350

Ser Thr Asp Asp Phe Leu Arg Tyr His Ser Ser Asn Ile Ile Asn Asp
                355                 360                 365

Ala Leu Tyr Val Asp Ile Lys Ala Asp Tyr Leu Arg Ala Gln Leu Ala
                370                 375                 380

Tyr Asp Leu Val Ser Leu Gly Thr Leu Thr Ser Asp Gln Gln Ser Ala
385                 390                 395                 400

Met Asp Met Met Thr Ser Gln Phe Glu Ser Leu Thr Leu Arg Tyr Asn
                405                 410                 415

Asn Tyr Lys Asp Ser Val Ala Ile Val Val Asp Tyr Ser Asn Thr Thr
                420                 425                 430

Met Ser Ala Thr Gln Ala Asp Phe Glu Ala Lys Leu Ala Ala Leu Pro
                435                 440                 445

Val Glu Val Gln Arg Ala Ile Ser Glu Leu Thr Ile Tyr Asp Gly Gln
                450                 455                 460

Ile Pro Gly Met Gly Glu Thr Thr Leu Gly Leu Ala Asn Ser Ala Asp
465                 470                 475                 480

Gln Thr Ile Ala Leu Lys Tyr Glu Ala Asn Asn Leu Asn Leu Val Ser
                485                 490                 495
```

```
Thr Val Leu His Glu Met Thr His Ile Ile Asp Phe Lys Ser Gly Leu
            500                 505                 510

Tyr Ser Glu Thr Thr Asp Arg Asn Thr Asp Gly Ser Leu Ser Thr Val
        515                 520                 525

Met Ala Phe Ser Asp Thr Gln Glu Phe Leu Asp Val Tyr His Thr Tyr
    530                 535                 540

Phe Asp Arg Pro Asp Val Trp Ser Tyr Tyr Arg Asp Asn Ser Glu Glu
545                 550                 555                 560

Ala Phe Ala Glu Gly Leu Ser Gln Tyr Ile Met His Arg Leu Phe Gly
                565                 570                 575

Thr Pro Tyr Ser Thr Tyr Ile Ala Asn Pro Tyr Thr Gly Asp Ala Tyr
            580                 585                 590

Asn Pro Gly Asp Gly Ser Gly Tyr Ser Pro Phe Ala Glu Thr Glu Phe
        595                 600                 605

Tyr Phe Ala Ser Leu Tyr Asn Arg Leu Phe Glu Tyr Pro Arg Thr Ala
    610                 615                 620

Gln Val Val Pro Tyr Leu Val Thr Thr Thr Thr Ala Pro Val Asn
625                 630                 635                 640

Gly Gln Val Ile Tyr Gly Ala Met Pro Glu Glu Thr Thr Thr Thr Thr
                645                 650                 655

Pro Tyr Thr Thr Val Tyr Val Gly Asp Thr Ser Phe Ala Tyr Asp Pro
            660                 665                 670

Thr Gly Gln Thr Asp Arg Val Gln Ala Gly Val Asp Gly Thr Glu Thr
        675                 680                 685

Ile Arg Thr Thr Tyr Ser Leu Asp Ser Asn Asn Gln Leu Val Ala Thr
    690                 695                 700

Gln Thr Val Ile Ser Ser Thr Pro Val Gln Asn Gln Ile Ile Thr Lys
705                 710                 715                 720

Gly Thr Gln Pro Thr Val Val Asp Thr Ser Val Pro Met Thr Ile Val
                725                 730                 735

Tyr Gln Glu Val Thr Asp Gly Ser Leu Gly Asp Trp Gln Val Asn Val
            740                 745                 750

Leu Asp Ala Gly Gln Asp Gly Leu Ile Arg Ser Thr Thr Thr Tyr Ser
        755                 760                 765

Val Asp Pro Val Thr Gly Ile Val Thr Pro Ser Thr Thr Glu Ala Thr
    770                 775                 780

Ile Thr Ala Met Arg Pro Met Ile Val Gln Tyr Gln Val Gly Ser Glu
785                 790                 795                 800

Lys Val Thr Ala Ile Pro Tyr Gln Thr Arg Tyr Val Ile Asp Thr Ser
                805                 810                 815

Leu Ala Thr Gly Thr Gln Val Ile Val Gln Glu Gly Val Asn Gly Ser
            820                 825                 830

Ser Thr Glu Ser Val Gln Ser Tyr Asn Phe Ile Gln Asp Gly Ser Asn
        835                 840                 845

Ser Arg Phe Asp Ala Ile Val Tyr Ala Ser Pro Val Val Ala Ala
    850                 855                 860

Gln Asp Gln Val Ile Ala Val Gly Gly Gln Asp Gln Val Thr Asp Gln
865                 870                 875                 880

Ala Val Ala Lys Thr Ile Phe Tyr Gln Glu Val Thr Asp Gly Ser Leu
                885                 890                 895

Gly Asp Trp Gln Val Lys Val Leu Asp Ala Gly Gln Asp Gly Leu Val
            900                 905                 910

Arg Thr Thr Thr Ser Tyr Ser Val Asp Pro Val Thr Gly Ile Val Thr
        915                 920                 925
```

```
Pro Ser Thr Thr Glu Ala Thr Ile Thr Ala Met Lys Pro Met Ile Val
        930                 935                 940

Gln Tyr Gln Val Gly Lys Ser Lys Leu Ser Ala Ile Pro Phe Leu Thr
945                 950                 955                 960

Glu Tyr Ile Thr Asp Asp Ser Leu Ala Val Gly Leu Glu Lys Val Ile
            965                 970                 975

Gln Glu Gly Val Gly Gly Thr Gln Ile Glu Thr Val Gln Ser Phe Asn
                980                 985                 990

Phe Ile Gln Asp Gly Ala Asn Ser His Phe Glu Asn Ile Val Tyr Ser
        995                 1000                1005

Ser Pro Thr Ile Val Val Ala Ala Val Asp Gln Val Ile Ala Arg
    1010                1015                1020

Gly Thr Lys Val Val Glu Val Val Ala Val Pro Glu Val Val
    1025                1030                1035

Thr Pro Lys Pro Glu Thr Ser Glu Val Ile Ser Pro Glu Lys Gly
    1040                1045                1050

Gln Thr Ala Pro Thr Ile Thr Val Glu Ala Ile Lys Ala Pro Ala
    1055                1060                1065

Gln Lys Lys Ala Lys Val Glu Val Val Thr Thr Pro Lys Glu Ser
    1070                1075                1080

Leu Pro Thr Thr Gly Asp Asp Gln Asn Leu Leu Val Thr Leu Met
    1085                1090                1095

Ser Ser Leu Leu Leu Met Ser Leu Gly Leu Gly Leu Lys Lys Lys
    1100                1105                1110

Glu Asp Glu
    1115

<210> SEQ ID NO 13
<211> LENGTH: 467
<212> TYPE: PRT
<213> ORGANISM: Streptococcus uberis

<400> SEQUENCE: 13

Leu Leu Ala Leu Ser Gln Leu Pro Asp Lys Leu Leu Glu Lys Ile Asp
1               5                   10                  15

Ile Thr Cys Phe Asp Asp Pro Lys His Phe Gly Arg Gly Ile Pro Phe
            20                  25                  30

Gln Glu Asp Ser Ser Thr Ala Trp Ile Asn Ser Pro Ile Asp Ala Ile
        35                  40                  45

Ser Tyr Asp Tyr His Asp Met Asn Asp Phe Gln Asn Trp Met Glu Gln
50                  55                  60

Lys Gly Leu Asp Thr Asp Gln Ser Tyr Val Pro Arg Ser Leu Tyr Gly
65                  70                  75                  80

Arg Tyr Met Thr Glu Arg Ala His Asp Leu Leu Gln Lys Leu Lys Ala
                85                  90                  95

Ser Val Ile His Glu Lys Val Thr Gln Leu Asn Tyr Glu Pro Asp Ser
            100                 105                 110

Gln Lys Trp Asn Ile Gly Thr Ser Gln Arg Thr Ile Pro Thr Arg Phe
        115                 120                 125

Asp Glu Val His Leu Thr Cys Gly Glu Leu Pro Val Leu Asp Pro Tyr
    130                 135                 140

His Leu Gln Gly Asn Pro Asn Tyr Ile Ala Asp Pro Tyr Pro Leu Lys
145                 150                 155                 160

Asn Leu Pro Lys Gln Pro Gly Lys Lys Asp Arg Ile Ala Ile Ile Gly
                165                 170                 175
```

```
Thr Gly Leu Ala Ser Ile Asp Thr Leu Lys Trp Leu Lys Asn Ser
            180                 185                 190

Gln Ala Asp Leu Leu Ala Phe Ser Pro Ser Met Thr Phe Pro Thr Val
        195                 200                 205

Arg Ile Leu Lys Lys Glu Thr Ile Asp Trp Gln Phe Leu Thr Asp Thr
        210                 215                 220

Asn Lys Gln Lys Leu Phe Glu Glu Asn Ser Phe Asn Phe Lys Ser Leu
225                 230                 235                 240

Glu Asn Leu Phe Leu Ser Leu Gln Ala Leu Gly Phe Gln Asn Trp
            245                 250                 255

Glu Glu Thr Cys Arg Gln Phe Leu Ala Glu Gly Ile Pro Gly Ile Ser
            260                 265                 270

Leu Ser Leu Ala Phe Pro Ala Gln Leu Phe Leu Gln Gln Leu Ala
            275                 280                 285

Ser His Leu Val Asp Trp Leu Thr Asp Phe Trp Pro Gln Met Thr Leu
            290                 295                 300

Ser Asp Arg Gln Tyr Tyr Lys Glu Asn Tyr Gly Lys Ala Ile Ile Asn
305                 310                 315                 320

Leu Arg Asn Pro Met Pro Glu Glu Ala Gly Arg Leu Ile Glu Ala
            325                 330                 335

Thr Ala Gln Gly Arg Leu Gln Ile Ile Glu Ala Val Thr Asp Ile Glu
            340                 345                 350

Ala Gly Asn Tyr Gly Phe Val Leu Lys Arg Glu Val Gly Lys Glu Leu
            355                 360                 365

Ser Val Ala Thr Val Ile Asn Ala Thr Gly Tyr His Leu Lys Glu Ser
370                 375                 380

Asn Val His Gln Ala Arg Thr Leu Ile Gln Val Ile Arg Asp Gly
385                 390                 395                 400

Leu Val Gln Ile Asn Pro Glu Gly Gly Leu Ser Ile Leu Pro Gln Thr
            405                 410                 415

Gly Gln Val Ile Ser Pro Lys Tyr Gly Ile Leu Ala Thr Leu Tyr Ala
            420                 425                 430

His Gly Ser Leu Val Asn Gly Val Ile Tyr Gln Asn Asn Ser Thr Ile
            435                 440                 445

Lys Ile Gln Gln Met Ala Glu Arg Ala Ile Gly Asn Val Ile Lys Lys
450                 455                 460

Pro Thr Ile
465

<210> SEQ ID NO 14
<211> LENGTH: 818
<212> TYPE: PRT
<213> ORGANISM: Streptococcus uberis

<400> SEQUENCE: 14

Met Arg Lys His Tyr Val Ser Lys Ser Ala Ile Phe Leu Ala Met Leu
1               5                   10                  15

Val Ala Thr Gly Ser Ala Gln Phe Val Lys Ala Glu Thr Pro Thr Thr
            20                  25                  30

Thr Thr Ser Pro Ala Thr Ser Leu Thr Asp Ala Ser Ala Ser Thr Thr
        35                  40                  45

Pro Thr Thr Asn Thr Thr Ser Thr Val Thr Pro Ala Leu Asp Pro Asn
    50                  55                  60

Thr Asn Phe Thr Val Asp Ser Ser Ala Thr Ser Thr Thr Thr Pro
65                  70                  75                  80
```

```
Ser Pro Val Glu Ala Ala Ile Ser Pro Val Ile Ala Thr Ala Gln
            85                  90                  95

Pro Thr Thr Asn Val Thr Ser Ala Ser Leu Ala Pro Ala Ala Asn Thr
                100                 105                 110

Met Ala Thr Thr Pro Val Glu Gly Gln Thr Val Asp Val Arg Ile Ile
            115                 120                 125

Ser Thr Thr Asp Leu His Ser Asn Leu Val Asn Tyr Asp Tyr Tyr Gln
130                 135                 140

Asp Lys Ala Ser Gln Thr Ile Gly Leu Ala Lys Ala Ala Val Leu Ile
145                 150                 155                 160

Asp Gln Ala Lys Ala Glu Asn Pro Asn Ala Val Leu Val Asp Asn Gly
                165                 170                 175

Asp Ile Leu Gln Gly Thr Pro Leu Gly Thr Tyr Glu Ala Leu Ile Asp
            180                 185                 190

Pro Leu Gln Pro Gly Glu Val His Pro Met Tyr Ala Ala Leu Asp Lys
            195                 200                 205

Leu Gly Phe Asp Ala Ser Thr Leu Gly Asn His Glu Phe Asn Tyr Gly
            210                 215                 220

Leu Thr Phe Ile Glu Asn Ala Ile Ala Ser Ala Gly Leu Pro Ile Leu
225                 230                 235                 240

Asn Ala Asn Val Phe Asp Ala Ala Thr Gly Glu Tyr Leu Phe Gln Pro
                245                 250                 255

Tyr Ala Ile Val Thr Lys Ser Phe Thr Asp Ala Asn Gly Gln Ala Val
            260                 265                 270

Asp Leu Lys Ile Gly Ile Thr Gly Ile Val Pro Pro Gln Ile Met Leu
            275                 280                 285

Trp Asp Lys Ala Asn Leu Glu Gly Lys Val Thr Val Lys Asp Ala Val
290                 295                 300

Gln Ala Val Thr Glu Ile Ile Pro Thr Ile Lys Asn Ala Gly Ala Asp
305                 310                 315                 320

Ile Val Leu Val Leu Ala His Thr Gly Ile Gly Asp Asp Val Tyr Glu
                325                 330                 335

Thr Gly Glu Glu Asn Val Gly Tyr Gln Ile Ala Ser Leu Ala Gly Val
            340                 345                 350

Asp Ala Val Val Thr Gly His Ser His Ala Glu Phe Pro Ser Gly Gln
            355                 360                 365

Asp Thr Gly Phe Tyr Glu Ser Tyr Asn Gly Val Asp Gly Val Ser Gly
            370                 375                 380

Leu Ile Asn Gly Thr Pro Val Thr Met Ala Gly Lys Tyr Gly Asp His
385                 390                 395                 400

Ile Gly Ile Ile Asp Leu Asn Val Ser Tyr Thr Gly Gly Lys Trp Thr
                405                 410                 415

Val Asn Arg Asp Lys Asn His Ala Glu Ile Arg Lys Ile Asp Thr Lys
            420                 425                 430

Ser Thr Ile Ala Asp Ala Asp Ile Leu Ala Leu Ala Gln Ala Ser His
            435                 440                 445

Leu Gly Thr Ile Asp Tyr Val Arg Gln Thr Val Gly Glu Thr Thr Ala
            450                 455                 460

Pro Ile Asn Ser Tyr Phe Ala Leu Val Lys Asp Asp Pro Ser Val Gln
465                 470                 475                 480

Ile Val Asn Asn Ala Gln Leu Trp Tyr Ala Lys Gln Gln Leu Ala Gly
                485                 490                 495

Thr Pro Glu Ala Asp Leu Pro Leu Leu Ser Ala Ala Ala Pro Phe Lys
            500                 505                 510
```

```
Ala Gly Thr Arg Asn Asp Pro Thr Ala Tyr Thr Asp Ile Pro Ala Gly
            515                 520                 525

Pro Ile Ala Ile Lys Asn Val Ala Asp Leu Tyr Leu Tyr Asp Asn Val
        530                 535                 540

Thr Ala Ile Leu Lys Leu Thr Gly Ala Asp Ile Lys Glu Trp Leu Glu
545                 550                 555                 560

Met Ser Ala Gly Gln Phe Asn Thr Ile Asp Pro Asn Val Ala Gly Pro
                565                 570                 575

Gln Asn Leu Val Asn Thr Asp Tyr Arg Thr Tyr Asn Phe Asp Val Ile
            580                 585                 590

Asp Gly Val Thr Tyr Glu Phe Asp Val Thr Gln Pro Asn Lys Tyr Asp
        595                 600                 605

Ala Lys Gly Asn Leu Leu Asn Pro Asn Ala Ser Arg Val Arg Asn Leu
    610                 615                 620

Lys Phe Gln Gly Lys Glu Ile Asp Pro Asn Gln Glu Phe Met Val Val
625                 630                 635                 640

Thr Asn Asn Tyr Arg Ala Ser Gly Ser Phe Pro Gly Val Lys Asn Ala
                645                 650                 655

Thr Ile Asn Arg Leu Leu Asn Leu Glu Asn Arg Gln Ala Ile Ile Asn
            660                 665                 670

Tyr Ile Val Ser Glu Lys Thr Ile Asn Pro Ser Ala Asp Asn Asn Trp
        675                 680                 685

Tyr Phe Ala Asp Thr Ile Gln Gly Leu Asp Leu His Phe Leu Ser Ala
    690                 695                 700

Asp Thr Ser Lys Asn Leu Ile Gly Asp Lys Ala Asp Ile Ser Tyr Thr
705                 710                 715                 720

Gly Pro Ser Thr Ile Glu Gly Phe Gly Asp Phe Val Phe Thr Tyr Val
                725                 730                 735

Lys Pro Glu Leu Pro Val Ala Thr Pro Glu Thr Pro Gln Glu Thr Gly
            740                 745                 750

Ser Gln Leu Thr Glu Asn Arg Arg Gln Glu Ile His Gln Leu Ala Thr
        755                 760                 765

Arg Val Tyr Asn Gln Thr Lys Ala Thr Ser Ser Ser Thr Thr Lys Ala
    770                 775                 780

Glu Leu Pro Lys Ala Gly Ser Gln Ser Lys Gly Leu Phe Phe Met
785                 790                 795                 800

Gly Leu Ser Leu Leu Gly Leu Ala Gly Leu Ile Thr Lys Lys Glu Glu
                805                 810                 815

Arg Gln

<210> SEQ ID NO 15
<211> LENGTH: 516
<212> TYPE: PRT
<213> ORGANISM: Streptococcus uberis

<400> SEQUENCE: 15

Met Arg Lys Phe Leu Met Ser Cys Phe Ala Ala Leu Leu Leu Leu Phe
1               5                   10                  15

Ala Gly Val Ser Gln Ala Asp Ala Asp Gln Tyr Leu Arg Val Gly Met
            20                  25                  30

Glu Ala Ala Tyr Ala Pro Phe Asn Trp Thr Gln Asp Asp Asn Ser Asn
        35                  40                  45

Gly Ala Val Pro Ile Glu Gly Thr Asn Gln Tyr Ala Asn Gly Tyr Asp
    50                  55                  60
```

-continued

```
Val Gln Val Ala Lys Lys Val Ala Lys Ser Leu Asn Lys Lys Leu Leu
 65                  70                  75                  80

Val Val Lys Thr Ser Trp Thr Gly Leu Ile Pro Ala Leu Thr Ser Gly
                 85                  90                  95

Lys Ile Asp Met Ile Ala Ala Gly Met Ser Pro Thr Glu Arg Lys
            100                 105                 110

Lys Glu Ile Ala Phe Ser Asp Ser Tyr Tyr Thr Ser Glu Pro Val Ile
            115                 120                 125

Val Val Lys Ala Asp Ser Lys Phe Ala Lys Ala Lys Ser Leu Asp Asp
130                 135                 140

Phe Ala Gly Ala Lys Ile Thr Ala Gln Gln Gly Val Trp His Val Asn
145                 150                 155                 160

Leu Ile Pro Gln Ile Asn Gly Val Lys Ala Gln Thr Pro Met Gly Asp
                165                 170                 175

Phe Ser Gln Met Arg Gln Ala Leu Ser Ser Gly Val Ile Asp Gly Tyr
                180                 185                 190

Ile Ser Glu Arg Pro Glu Ala Met Thr Ala Glu Asn Ala Asn Ser Ala
                195                 200                 205

Phe Lys Met Val Val Leu Lys Lys Ala Phe Thr Val Asn Glu Ser Asp
210                 215                 220

Ala Ala Ile Ala Val Gly Met Arg Lys Asp Asp Pro Arg Ile Val Gln
225                 230                 235                 240

Val Asn Thr Val Leu Ala Asp Leu Ser Ala Asn Asp Arg Leu Asp Leu
                245                 250                 255

Met Asp Lys Met Val Thr Leu Gln Pro Lys Glu Lys Lys Ala Glu Asn
                260                 265                 270

Gly Val Gln Pro Ser Phe Leu Asp Gln Met Trp Ser Ile Val Thr Lys
                275                 280                 285

Asn Trp Lys Gln Phe Leu Arg Gly Thr Gly Leu Thr Leu Leu Ile Ser
290                 295                 300

Thr Ile Gly Thr Ile Val Gly Leu Ile Ile Gly Leu Leu Ile Gly Ile
305                 310                 315                 320

Tyr Arg Thr Ala Pro Lys Ser Lys His Lys Val Leu Ala Phe Phe Gln
                325                 330                 335

Lys Leu Phe Gly Trp Phe Leu Asn Val Tyr Ile Glu Val Phe Arg Gly
                340                 345                 350

Thr Pro Met Ile Val Gln Ser Met Val Ile Tyr Tyr Gly Thr Ala Gln
                355                 360                 365

Ala Phe Gly Ile Ser Ile Asp Arg Thr Leu Ala Ala Ile Phe Ile Val
                370                 375                 380

Ser Ile Asn Thr Gly Ala Tyr Met Thr Glu Ile Val Arg Gly Gly Ile
385                 390                 395                 400

Phe Ala Val Asp Lys Gly Gln Phe Glu Ala Thr Ala Leu Gly Phe
                405                 410                 415

Thr His Gly Gln Thr Met Arg Lys Ile Val Leu Pro Gln Val Val Arg
                420                 425                 430

Asn Ile Leu Pro Ala Thr Gly Asn Glu Phe Val Ile Asn Ile Lys Asp
                435                 440                 445

Thr Ser Val Leu Asn Val Ile Ser Val Val Glu Leu Tyr Phe Ser Gly
450                 455                 460

Asn Thr Val Ala Thr Gln Asn Tyr Gln Tyr Phe Gln Thr Phe Ser Val
465                 470                 475                 480

Ile Ala Val Ile Tyr Phe Ile Leu Thr Phe Thr Val Thr Arg Ile Leu
                485                 490                 495
```

```
Arg Tyr Val Glu Arg Ile Asp Asp Asp Asn Tyr Thr Thr Thr Val
            500                 505                 510

Asn Glu Leu Pro
       515
```

```
<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gctcttcgga ttttcggtat c                                              21

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
cattttccac gaatagaagg actgtc                                         26

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tggttgaagc agaagctgaa                                                20

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
gagcaattgc aaaatgaaaa gc                                             22

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
atgtcaaaag cccggtacct ttacag                                         26

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
gaaatgatga tgagaaattg aga                                            23
```

-continued

```
<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
agccacaaac accattcaca                                           20

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
gaagaagtgg taactgctac aaac                                      24

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
tactaacttc ttgtcatctt ggtacctttt                                30

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
caacgaatca acaaactgaa agc                                       23
```